(12) United States Patent
Abrignani et al.

(10) Patent No.: US 7,097,987 B2
(45) Date of Patent: Aug. 29, 2006

(54) HEPATITIS C RECEPTOR PROTEIN CD81

(75) Inventors: Sergio Abrignani, Vagliagli (IT); Guido Grandi, Segrate (IT)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/859,700

(22) Filed: Jun. 3, 2004

(65) Prior Publication Data

US 2004/0258694 A1 Dec. 23, 2004

Related U.S. Application Data

(63) Continuation of application No. 09/509,612, filed as application No. PCT/IB98/01628 on Oct. 6, 1998, now abandoned.

(30) Foreign Application Priority Data

Oct. 6, 1997 (GB) .................. 9721182.5
Jun. 23, 1998 (GB) .................. 9813560.1

(51) Int. Cl.
*G01N 33/53* (2006.01)
*C12Q 1/70* (2006.01)
*A61K 38/16* (2006.01)
*C07K 14/705* (2006.01)

(52) U.S. Cl. .................. 435/7.1; 435/4; 435/5; 435/7.2; 435/7.21; 530/300; 530/350; 514/2

(58) Field of Classification Search ................ 530/300, 530/350, 412; 514/2; 435/5, 7.1, 69.1, 69.3, 435/7.2, 7.21; 424/189.1, 204.1, 228.1
See application file for complete search history.

(56) References Cited

FOREIGN PATENT DOCUMENTS

| EP | 0318216 A1 | 5/1989 |
|---|---|---|
| EP | 0388232 A1 | 9/1990 |
| WO | WO 96/05513 | 2/1996 |
| WO | WO 97/09349 | 3/1997 |

OTHER PUBLICATIONS

Wright et al., Immunology Today, vol. 15 No. 12, pp. 588-594 (1994).*
Levy et al., Journal of Biological Chemistry, vol. 266 No. 22, pp. 14597-14602 (Aug. 1991).*
Andria et al., "Genomic Organization and Chromosomal Localization of the TAPA-1 Gene," *Journal of Immunology* 147(3):1030-1036 (1991).
Berditchevski et al., "Characterization of Novel Complexes on the Cell Surface Between Integrins and Proteins with 4 Transmembrane Domains (TM4 Proteins)," *Mol. Biol. Cell* 7:193-207 (1996).
Blight et al., "Detection and Distribution of Hepatits C-Specific Antigen in Naturally Infected Liver" *Hepatology*, 20:553-557 (1994).
Bouffard et al., "Hepatitis C Virus is Detected in a Monocyte/Macrophage Subpopulation of Peripheral Blood Mononuclear Cells of Infected Patients". J. Infect. Dis., 166:1276-1280 (1992).
Bradbury et al., "The CDl9/CD21 Signal Transducing Complex of Human B Lymphocytes Includes the Target of Antiproliferative Antibody-1 and Leu-13 Molecules," *J. Immunol.* 149(9):2841-2850 (1991).
Campbell et al., "Folate-binding Protein is a Marker for Ovarian Cancer," *J. Cancer Res.*, 51:5329-5338 (1991).
Chomczinsky et al., "Single-Step Method of RNA Isolation by Acid Guanidinium Thiocyanate-Phenol-Chloroform Extraction", *Anal. Biochem.*, 162:156-159 (1987).
Choo, "Vaccination of Chimpanzees against infection by the Hepatitis C Virus", Proc. Natl. Acad. Sci. USA, 91:1294 (1994).
Cooper, "Immunobiology of CR2, the B Lymphocyte Receptor for Epstein-Barr Virus and the C3d Complement Fragment", *Annu. Rev. Immunol.*, 6:85-113 (1988).
Dailey et al., "Sequences in the Polyomavirus DNA Regulatory Region Involved in Viral DNA Replication and Early Gene Expression", J. Virol 54:739-749 (1985).
Fearon, D.T., and Carter, R.H., "The CD19/CR2/TAPA-1 Complex of B Lymphocytes: Linking Natural to Acquired Immunity," *Annu. Rev. Immunol.* 13:127-149 (1995).
Guan et al., "Eukaryotic Proteins Expressed in *Escherichia coli*: An Improved Thrombin Cleavage and Purification Procedure of Fusion Proteins with Glutathione S-Transferase", Anal. Biochem., 192:262-267 (1991).
Levy et al., "CD81 (TAPA-1): A Molecule Involved in Signal Transduction and Cell Adhesion in the Immune System," *Annu. Rev. Immunol.* 16:89-109 (1998).
Mannion et al., Transmembrane-4 Superfamily Proteins CD81 (TAPA-1), CD82, CD63 and CD53 Specifically Associated with Integrin (CD49d/CD29), J. Immunol., 157:2039 (1996).
Oren et al., "Tapa-1, the Target of an Antiproliferative Antibody, Defines a New Family of Transmembrane Proteins," *Molecular and Cellular Biology* 10(8):4007-4015 (1990).
Pileri et al., "Binding of Hepatitis C Virus to CD81," *Science* 282:938-941 (1998).
Rosa, D. et al., "A Quantitative Test to Estimate Neutralizing Antibodies to the Hepatitis C Virus: Cytofluorimetric Assessment of Envelope Glycoprotein 2 Binding to Target Cells," *Proc. Natl. Acad. Sci. U.S.A.* 93(3):1759-1763 (1996).

* cited by examiner

*Primary Examiner*—James C. Housel
*Assistant Examiner*—Zachariah Lucas
(74) *Attorney, Agent, or Firm*—Roberta L. Robins; Michael J. Moran; Alisa A. Harbin

(57) ABSTRACT

The present invention relates to the use of CD81 protein and polynucleic acid in the therapy and diagnosis of hepatitis C and pharmaceutical compositions, animal models and diagnostic kits for such purposes.

2 Claims, 17 Drawing Sheets

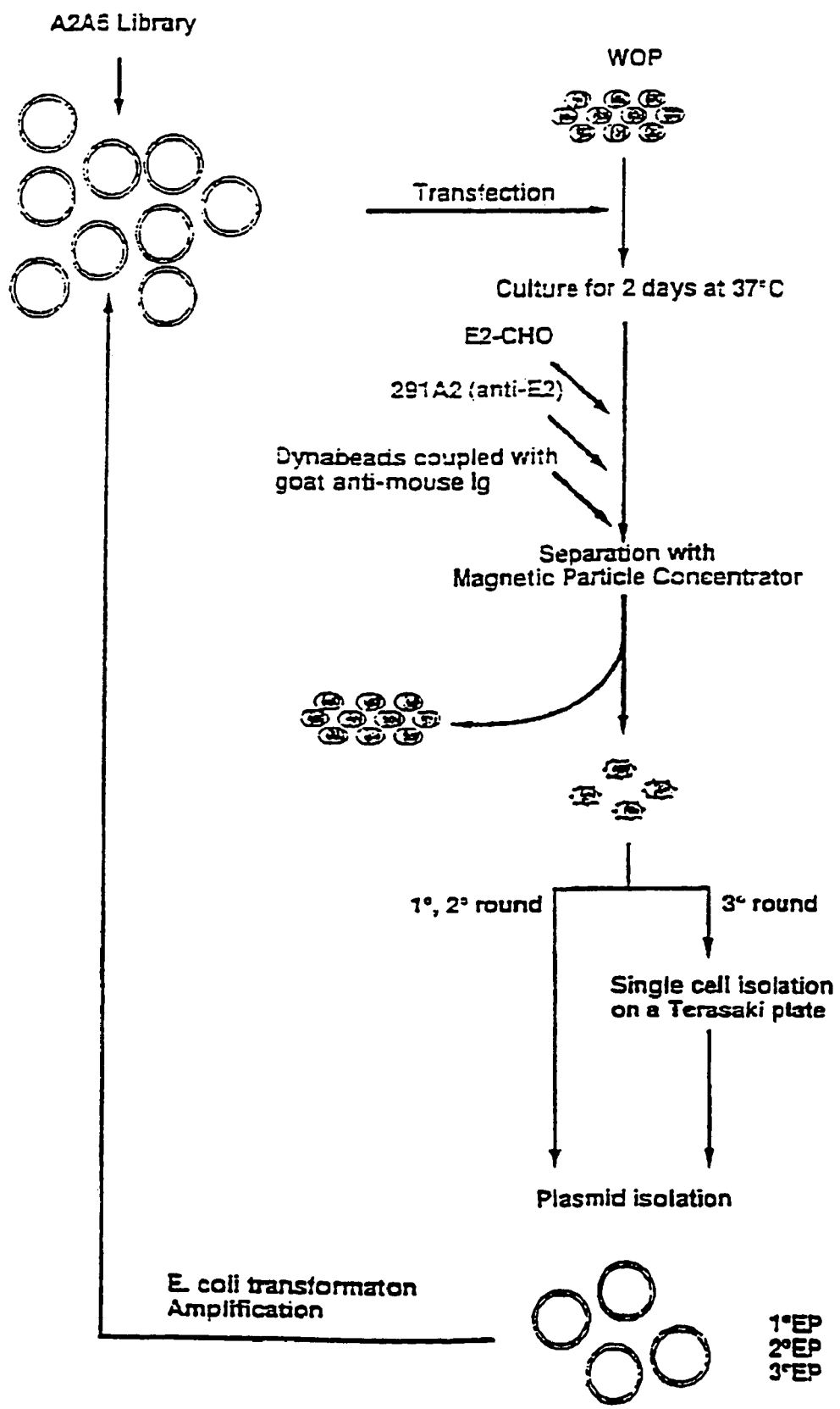
FIG. 1A 1°, 2°, 3° round screening

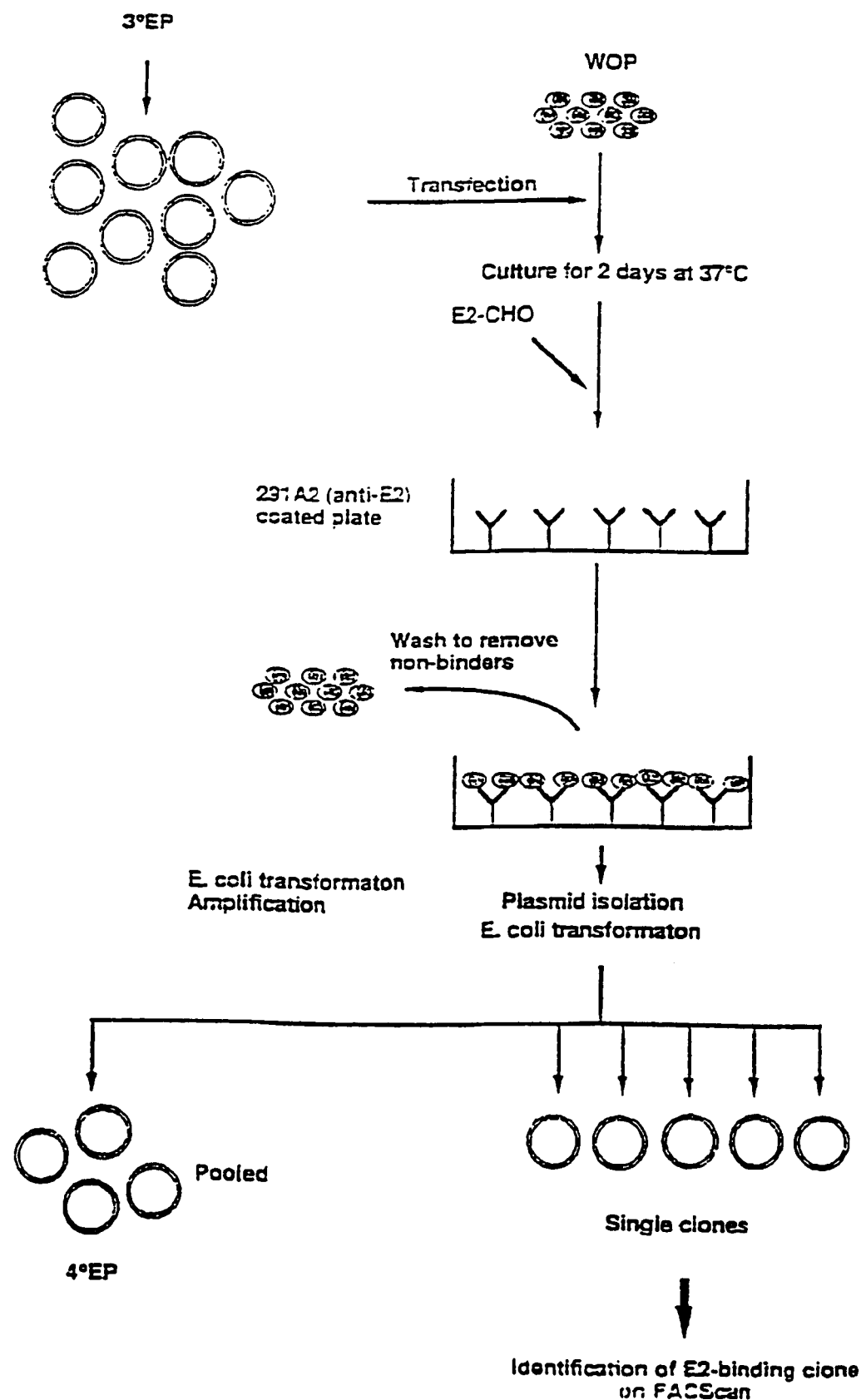
FIG. 1B  4° round screening

HEPATITIS C RECEPTOR PROTEIN CD81

CROSS-REFERENCE TO RELATED APPLICATIONS

This application is a continuation of U.S. patent application Ser. No. 09/509,612, filed Mar. 29, 2000 now abandoned, which is a 371 of PCT/IB98/01628, filed Oct. 6, 1998, which claims priority to GB9721182.5, filed Oct. 6, 1997 and GB9813560.1, filed Jun. 23, 1998, from which applications priority is claimed pursuant to the provisions of 35 U.S.C. §119 and §120, which applications are incorporated herein by reference in their entireties.

FIELD OF THE INVENTION

The present invention relates to the use of CD81 protein and nucleic acid encoding this protein in the therapy and diagnosis of hepatitis C and to pharmaceutical compositions, animal models and diagnostic kits for such uses.

Brief Description of the Prior Art

All publications, manuals, patents, and patent applications cited herein are incorporated in full by reference. HCV (previously known as Non-A Non-B hepatitis—NANBV) is a positive sense RNA virus of about 10000 nucleotides with a single open reading frame encoding a polyprotein of about 3000 amino acids. Although the structure of the virus has been elucidated by recombinant DNA techniques (European patent application EP-A-0318216 and European patent application EP-A-0388232), the virus itself has not been isolated and the functions of the various viral proteins produced by proteolysis of the polyprotein have only been inferred by analogy with other similar viruses of similar genomic organisation (Choo et al PNAS USA (1991)88 2451–2455).

The viral proteins are all available in recombinant form expressed in a variety of cells and cell types including yeast, bacteria, insect, plant and mammalian cells (Chien, D. Y. et al PNAS USA (1992) 89 10011–10015 and Spaete. R. R. et al Virology (1992) 188 819–830).

Two proteins, named E1 and E2 (corresponding to amino acids 192–383 and 384–750 of the HCV polyprotein respectively) have been suggested to be external proteins of the viral envelope which are responsible for the binding of virus to target cells.

HCV research is hindered very considerably by the limited host range of the virus. The only reliable animal model for HCV infection is the chimpanzee and HCV does not readily propagate in tissue culture.

In our copending International patent application PCT/IB95/00692 (WO 96/05513), we describe a method employing flow cytometry to identify cells carrying the HCV receptor. We have shown that by labelling cells with recombinant E2 envelope protein, it is possible to sort cells using flow cytometry, isolating those cells capable of specific binding to the E2 and therefore potentially carrying an HCV receptor.

In our copending International patent application PCT/IB96/00943 (WO 97/09349), we have identified a protein capable of binding to the E2 envelope protein of HCV.

We have now succeeded with some difficulty in cloning the DNA encoding the HCV receptor and have discovered, surprisingly that the DNA encodes a cellular protein known as CD81. We are not aware of any association in the literature between CD81 and the HCV. CD81 was first identified by monoclonal antibodies as the target of an antiproliferative antibody (TAPA-1) which inhibited in vitro cellular proliferation. Armed with this new information and given the sequence knowledge of CD81 in the public databases it is now possible to design and produce an armoury of therapeutic and diagnostic reagents against HCV.

SUMMARY OF THE INVENTION

According to the present invention, there is provided a CD81 protein, or functional equivalent thereof, for use in the therapy or diagnosis of hepatitis C(HCV). According to a further aspect of the present invention there is provided a compound that binds specifically to the CD81 protein for use in the therapy or diagnosis of HCV.

The term "CD81 protein, or a functional equivalent thereof" as used herein means the human CD81 protein as defined by the protein sequence listed in the SWISSPROT database (Accession No. P18582) or the EMBL/GENBANK database (Accession No. M33690) or a functional equivalent thereof. A functional equivalent of CD81 is a compound which is capable of binding to HCV, preferably to the E2 protein of HCV. Preferably, the functional equivalent is a peptide or protein. The term "functional equivalent" includes an analogue of CD81, a fragment of CD81, and CD81 mutants and muteins.

One region of the human CD81 protein that is shown herein to be involved in binding to the E2 protein of HCV is the "EC2" region comprising amino acids 113–201 of the full length human sequence shown in FIG. 1. The invention encompasses proteins and protein fragments containing this region of human CD81, or containing functional equivalents of this region, such as, for example, the Chimpanzee sequence identified in FIG. 1. Preferably, the functional equivalent is at least 80% homologous to the human CD81 sequence across the EC2 region of the protein, preferably at least 90% homologous as assessed by any conventional analysis algorithm such as for example, the Pileup sequence analysis software (Program Manual for the Wisconsin Package, 1996).

The term "a functionally equivalent fragment" as used herein also means any fragment or assembly of fragments of the complete protein that binds to HCV, preferably that binds to the E2 protein of HCV. The complete protein may be truncated at one or both ends or domains may be removed internally provided that the protein retains the defined function. For example, one or more regions of the protein responsible for membrane binding (TM1 to TM4 in FIG. 1) may be removed to render the protein soluble when produced by a recombinant process. The fragment of choice comprises the extracellular loop 2 (EC2 in FIG. 1) of the CD81 protein (amino acids 113–201).

If proteinaceous, functionally equivalent fragments or analogues may belong to the same protein family as the human CD81 protein identified herein. By "protein family" is meant a group of proteins that share a common function and exhibit common sequence homology. By sequence homology is meant that the protein sequences are related by divergence from a common ancestor, such as is the case between the human and the chimpanzee. Chimpanzee CD81 is thus an example of a functionally equivalent protein that binds to HCV.

Preferably, the homology between functionally equivalent protein sequences is at least 25% across the whole of amino acid sequence of the complete protein or of the complete EC2 fragment (amino acids 113–201). More preferably, the homology is at least 50%, even more preferably 75% across the whole of amino acid sequence of the protein or protein fragment. Most preferably, homology is greater than 80% across the whole of the sequence.

The term "a functionally equivalent analogue" is used to describe those compounds that possess an analogous function to an activity of the CD81 protein and may, for example comprise a peptide, cyclic peptide, polypeptide, antibody or antibody fragment. These compounds may be proteins, or may be synthetic agents designed so as to mimic certain structures or epitopes on the inhibitor protein. Preferably, the compound is an antibody or antibody fragment.

The term "functionally equivalent analogue" also includes any analogue of CD81 obtained by altering the amino acid sequence for example by one or more amino acid deletions, substitutions or additions such that the protein analogue retains the ability to bind to HCV, preferably the E2 protein of HCV. Amino acid substitutions may be made, for example, by point mutation of the DNA encoding the amino acid sequence.

The functional equivalent of CD81 may be an analogue of a fragment of CD81. The CD81 or functional equivalent may be chemically modified, provided it retains its ability to bind to HCV, preferably the E2 protein of HCV.

It is envisaged that such molecules will be extremely useful in preventative therapy of HCV infection, because these molecules will bind specifically to the virus and will thus prevent internalisation of the virus into cells. As used herein, "binding specifically" means that the functionally equivalent analogue has high affinity for the E2 protein of the HCV virus and does not bind to any other protein with similar high affinity. Specific binding may be measured by a number of techniques such as Western blotting, FACS analysis, or immunoprecipitation. Preferably, the functionally equivalent analogue binds to the E2 protein with an affinity of at least $10^{-8}$, preferably at least $10^{-9}$ and most preferably greater than $10^{-10}$.

According to a further embodiment of the invention there is provided a compound that binds to CD81, such as a monoclonal or polyclonal antibody to CD81, for use in the diagnosis or therapy of HCV. Preferably the compound binds specifically to CD81 with an affinity of at least $10^{-8}$, preferably at least $10^{-9}$ and most preferably greater than $10^{-10}$. Such compounds may be used to prevent the virus binding to patient cells and being internalised.

The CD81 molecule is present on a number of different cell types. Ideally, the compound that binds to CD81 therefore only interacts with CD81 in the presence of. HCV, so that the usual function of CD81 is not compromised on healthy cells. Antibodies and suitable methods of screening for such antibodies are described in co-pending applications EP 96928648.3 and EP 95927918.3.

The CD81 protein, or functional equivalent thereof may be produced by any suitable means, as will be apparent to those of skill in the art. In order to produce sufficient amounts of CD81 protein or functional equivalents thereof for use in accordance with the present invention, expression may conveniently be achieved by culturing under appropriate conditions recombinant host cells containing the CD81 protein, or functional equivalent thereof.

Systems for cloning and expression of a polypeptide in a variety of different host cells are well known.

Two preferred methods of construction of carrier proteins according to the invention are direct chemical synthesis and by production of recombinant protein. Preferably, the CD81 protein is produced by recombinant means by expression from an encoding nucleic acid molecule. Recombinant expression has the advantage that the production of the protein is inexpensive, safe, facile and does not involve the use of toxic compounds that may require subsequent removal.

When expressed in recombinant form, the CD81 protein or functional equivalent thereof is preferably generated by expression from an encoding nucleic acid in a host cell. Any host cell may be used, depending upon the individual requirements of a particular system. Suitable host cells include bacteria, mammalian cells, plant cells, yeast and baculovirus systems. Mammalian cell lines available in the art for expression of a heterologous polypeptide include Chinese hamster ovary cells. HeLa cells, baby hamster kidney cells and many others. Preferably, bacterial hosts are used for the production of recombinant protein, due to the ease with which bacteria may be manipulated and grown. A common, preferred bacterial host is E. coli.

Preferably, if produced recombinantly, the CD81 protein or functional equivalent is expressed from a plasmid that contains a synthetic nucleic acid insert. The insertion site in the expression plasmid into which the nucleic acid encoding the CD81 protein or functional equivalent is cloned may allow linkage of the protein to a tag, such as the "flag" peptide or polyhistidine. This arrangement facilitates the subsequent purification of recombinant protein.

According to a further aspect of the present invention, there is also provided a nucleic acid molecule encoding the CD81 protein or functional equivalent thereof, for use in the therapy or diagnosis of HCV infection. Preferably, the nucleic acid encodes human CD81 protein. As will be apparent to one of skill in the art, such a nucleic acid molecule will be designed using the genetic code so as to encode the protein or peptide that is desired. A nucleic acid molecule according to this aspect of the present invention may comprise DNA, RNA or cDNA and may additionally comprise nucleotide analogues in the coding sequence. Preferably, the nucleic acid molecule will comprise DNA.

Nucleotide sequences included within the scope of this embodiment of the invention are those hybridising to nucleic acid encoding the CD81 protein under standard conditions. As used herein, standard conditions includes both non-stringent standard hybridisation conditions (6×SSC/50% formamide at room temperature) with washing under conditions of low stringency (2×SSC/50% formamide at room temperature or 2×SSC, 42° C.) or at standard conditions of higher stringency, e.g. 2×SSC, 65° C. (where SSC=0.15 M NaCl, 0.015 M sodium citrate, pH 7.2). Preferably the term standard conditions refers to conditions of high stringency.

Preferably, such nucleic acid molecules will retain the ability to hybridise specifically to nucleic acid encoding CD81 or a fragment thereof and will include nucleic acid sequences with 40% homology across the whole of the human CD81 gene sequence as defined by the Pileup command of the GCG Program manual for the Wisconsin Package (version 9, 1996). More preferably, the homology is at least 65% across the whole of the gene sequence. Most preferably, homology is greater than 70% across the whole of the gene sequence.

Nucleic acid encoding the CD81 protein or functional equivalent may be cloned under the control of an inducible promoter, so allowing precise regulation of protein expression. Suitable inducible systems will be well known to those of skill in the art.

Suitable vectors for the expression of the CD81 protein or functional equivalent may be selected from commercial sources or constructed in order to suit a particular expression system. Such vectors will contain appropriate regulatory sequences, such as promoter sequences, terminator sequences, polyadenylation sequences, enhancer sequences and marker genes. Vectors may be plasmids or viral-based. For further details see Molecular Cloning: a laboratory manual (Sambrook et al. 1989). Many known techniques and protocols for the manipulation of nucleic acids and analysis of proteins are described in detail in "Short protocols in molecular biology"second addition, Ausubel et al. (John Wiley & Sons 1992).

Methods for the isolation and purification of recombinant proteins will be well known to those of skill in the art and are summarised, for example in Sambrook et al (1989).

Particularly in bacteria such as *E. coli*, the recombinant protein will form inclusion bodies within the bacterial cell, thus facilitating its preparation. If produced in inclusion bodies, the carrier protein may need to be refolded to its natural conformation.

Additionally, in order to tailor precisely the exact properties of the CD81 protein or functional equivalent thereof the skilled artisan will appreciate that changes may be made at the nucleotide level from known CD81 sequences, by addition substitution, deletion or insertion of one or more nucleotides. Site-directed mutagenesis (SDM) is the method of preference used to generate mutated proteins according to the present invention. There are many techniques of SDM now known to the person of skill in the art, including Oligonucleotide-directed mutagenesis using PCR as set out, for example by Sambrook et al., (1989) or using commercially available kits.

Suitable vectors can be chosen or constructed, containing appropriate regulatory sequences, including promoter sequences, terminator sequences polyadenylation sequences enhancer sequences marker genes and other sequences as appropriate. Vectors may be plasmids, viral e.g. phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition. Ausubel et al. eds., John Wiley & Sons, 1992. The disclosures of Sambrook et al. and Ausubel et al. are incorporated herein by reference.

According to a further aspect of the invention, there is provided a method for treating an infection of HCV comprising administering to a patient a therapeutically effective amount of CD81 protein, or a functional equivalent thereof effective to reduce the infectivity of the virus.

Since the infection mechanism of HCV appears to depend, in part, upon the availability of a cell surface receptor, making available a soluble form of the CD81 protein, or a functional equivalent thereof will act as an antagonist of binding of HCV to the cellular receptor thus reducing or preventing the infection process and thereby treating the disease.

A suitable soluble form of the CD81 protein, or a functional equivalent thereof might comprise, for example, a truncated form of the protein from which one or more of the transmembrane domain or domains TM1–TM4 have been removed either by a protein cleavage step or by design, in a chemical or recombinant DNA synthesis. The preferred soluble form of the protein comprises the EC2 domain (residues 113–201 as identified in FIG. 1). The EC1 domain may act to increase the affinity or specificity of the protein for HCV.

Alternatively, a hybrid particle comprising at least one particle-formiing protein, such as hepatitis B surface antigen or a particle-forming fragment thereof, in combination with the CD81 protein or functional equivalent thereof could be used as an antagonist of binding of HCV to the cellular receptor.

According to a still further aspect of the invention, there is provided a method for treating an infection of HCV comprising administering to a patient a therapeutically effective amount of a compound that specifically binds to CD81 protein, such as a monoclonal antibody directed to CD81. The rationale behind this therapeutic strategy is that the binding of the cell surface receptor to another compound will prevent the binding of HCV to the receptor, so preventing the infection process and thereby treating the disease.

According to a further aspect of the invention, there is provided a pharmaceutical composition comprising a CD81 protein or functional equivalent thereof, optionally as a pharmaceutically acceptable salt, in combination with a pharmaceutically acceptable carrier. According to a still further aspect of the present invention there is provided a pharmaceutical composition comprising a compound that binds specifically to the CD81 protein optionally as a pharmaceutically acceptable salt, in combination with a pharmaceutically acceptable carrier.

The pharmaceutical composition may be in any appropriate form for administration including oral, parenteral transdermal and transcutaneous compositions. The composition may be administered alone or in combination with other treatments, either simultaneously or sequentially dependent upon the condition to be treated.

A process is also provided for making the pharmaceutical composition, in which a protein of the present invention is brought into association with a pharmaceutically acceptable carrier.

According to a further aspect of the invention, there is provided a CD81 protein or functional equivalent thereof or a compound that binds specifically to the CD81 protein for use as a pharmaceutical.

According to a further aspect of the invention, there is provided the use of a CD81 protein or functional equivalent thereof or compound that binds specifically to the CD81 protein in the manufacture of a medicament for the treatment of an HCV infection.

The ability of a CD81 protein or functional equivalent thereof to bind to HCV permits the use of the protein as a diagnostic for HCV infection for example in an ELISA (Enzyme linked immunosorbent assay) or RIA (Radioimmunoassay).

A soluble form of the protein could, for example, be used in an ELISA form of assay to measure neutralising antibodies in serum. More preferably, antibodies to CD81 will be suitable for use in this context, since these molecules will be anti-idiotypic antibodies for HCV itself.

According to a further aspect of the invention, there is provided an assay for HCV antibodies in a serum sample comprising the step of allowing competitive binding between antibodies in the sample and a known amount of an HCV protein for binding to a CD81 protein or functional equivalent thereof and measuring the amount of the known HCV protein bound.

Preferably, the CD81 protein or functional equivalent thereof is immobilised on a solid support and the HCV protein, which may suitably be E2 HCV envelope protein, optionally recombinant E2 protein is labelled. The label may be a radioactive label, a peptide, an epitope, an enzyme or any other bioactive compound. Preferably the label comprises an enzyme.

In an assay of this form, competitive binding between antibodies and the HCV protein for binding to the CD81 protein or functional equivalent thereof results in the bound HCV protein being a measure of antibodies in the serum sample, most particularly, HCV neutralising antibodies in the serum sample.

A significant advantage of the assay is that direct measurement is made of neutralising of binding antibodies (i.e. those antibodies which interfere with binding of HCV envelope protein to the cellular receptor). Such an assay, particularly in the form of an ELISA test has considerable applications in the clinical environment and in routine blood screening.

Also, since the assay measures nreutralising of binding antibody titre, the assay forms a ready measure of putative vaccine efficacy, neutralising of binding antibody titre being correlated with host protection.

In a further aspect of the invention, there is provided a diagnostic kit comprising the CD81 protein or functional equivalent thereof. Preferably the kit also contains at least one labelled HCV protein, optionally enzyme labelled. The kit will also contain other components necessary for the analysis of the presence of HCV or anti-HCV antibodies in serum. Such components will be readily apparent to those of skill in the art.

The CD81 protein or functional equivalent thereof may be used to screen for chemical compounds mimicking the HCV surface structure responsible for binding to the HCV receptor.

According to a further aspect of the invention, there is provided a method for screening chemical compounds for ability to bind to the region of HCV responsible for binding to a host cell, comprising measuring the binding of a chemical compound to be screened to a CD81 protein or functional equivalent thereof. The host cell may be any mammalian cell, preferably a human host cell.

This aspect of the invention encompasses the products of the screening process whether alone, in the form of a pharmaceutically acceptable salt, in combination with one or more other active compounds and/or in combination with one or more pharmaceutically acceptable carriers. Processes for making a pharmaceutical composition are also provided in which a chemical compound identified by the process of the invention is brought into association with a pharmaceutically acceptable carrier.

The chemical compound may be an organic chemical and may contain amino acids or amino acid analogues. Preferably however the chemical compound is a peptide, polypeptide or a polypeptide which has been chemically modified to alter its specific properties such as the affinity of binding to the CD81 protein or functional equivalent thereof or its stability in vivo.

According to a further aspect of the invention, there is provided a nucleic acid encoding CD81 protein or functional equivalent thereof for use in diagnosis or therapy of HCV. The nucleic acid may encode any part of the CD81 protein, or functional equivalent thereof. Preferably, the nucleic acid encodes a portion of CD81 that binds to HCV E2. According to a still further aspect of the present invention, there is provided a nucleic acid encoding a peptide or polypeptide compound that binds specifically to CD81.

Changes to the nucleic acid may be made at the nucleotide level by addition, substitution, deletion or insertion of one or more nucleotides, which changes may or may not be reflected at the amino acid level, dependent on the degeneracy of the genetic code.

The nucleic acid may be included in a vector, optionally an expression vector permitting expression of the nucleic acid in a suitable host to produce CD81 protein or functional equivalent thereof.

The identification of the DNA encoding the HCV receptor, namely CD81, makes available the full power of molecular biology for the molecular analysis of HCV and in particular its infectious mechanism offering for the first time the possibility of designing methods of treating the virus. PCR methods may be used to identify cells carrying the receptor and DNA molecules may be designed to act as polymerase chain reaction (PCR) primers in this connection. Although CD81 is widespread and is associated with normal human function the present invention includes antisense molecules inhibiting CD81 production for use in the treatment of HCV and in the manufacture of a medicament for the treatment of HCV infection.

The identification of polymorphisms in the CD81 protein may be found to be associated with susceptibility to HCV infection or likely prognosis. Accordingly, the identification of the gene encoding the HCV receptor allows the evaluation of polymorphisms present throughout the human population.

According to a further aspect of the invention there is provided an antibody to CD81 protein or functional equivalent thereof for use in the treatment of an HCV infection and in the manufacture of a medicament for the treatment of an HCV infection. The antibody is preferably a monoclonal antibody. Such an antibody can be used to temporarily block the CD81 receptor preventing infection from HCV, for example, immediately after an accidental infection with HCV-infected blood.

At present, the only available animal model of HCV infection is the chimpanzee, which is a protected species. Experiments on such animals pose a number of difficulties which together result in a very considerable expense (a one year experiment with one chimpanzee can cost $70,000). Compared to this a mouse model would be far more acceptable. Unfortunately, as described below, the HCV receptor, whilst ubiquitous in humans and found in chimpanzees, is absent in other mammals. A transgenic mammal, for example a mouse, carrying the HCV receptor on the cell surface, perhaps expressed in greater or lesser amounts than normally found, would be of great benefit to HCV research and the development of vaccines. Expression of mutant CD81 proteins on the surface of cells would also be a useful research tool.

According to a further aspect of the invention, there is provided a transgenic non-human animal, suitably a mammal such as a mouse, carrying a transgene encoding a CD81 protein or functional equivalent thereof.

The transgenic animal of the invention may carry one or more other transgenes to assist in maintaining an HCV infection.

There is also provided a process for producing a transgenic animal comprising the step of introducing a DNA encoding a CD81 protein or functional equivalent thereof into the embryo of a non-human mammal, preferably a mouse. Preferably the CD81 protein or functional equivalent thereof is a human CD81 protein.

According to a further aspect of the present invention, there is provided a CD81 protein or a functional equivalent thereof for use as a protective immunogen in the control of HCV.

BRIEF DESCRIPTION OF THE DRAWINGS

FIG. 1A is a schematic description of primary, secondary and tertiary rounds of screening.

FIG. 1B is a schematic description of the final round of screening.

DETAILED DESCRIPTION OF THE INVENTION

EXAMPLE 1

Figure 1:
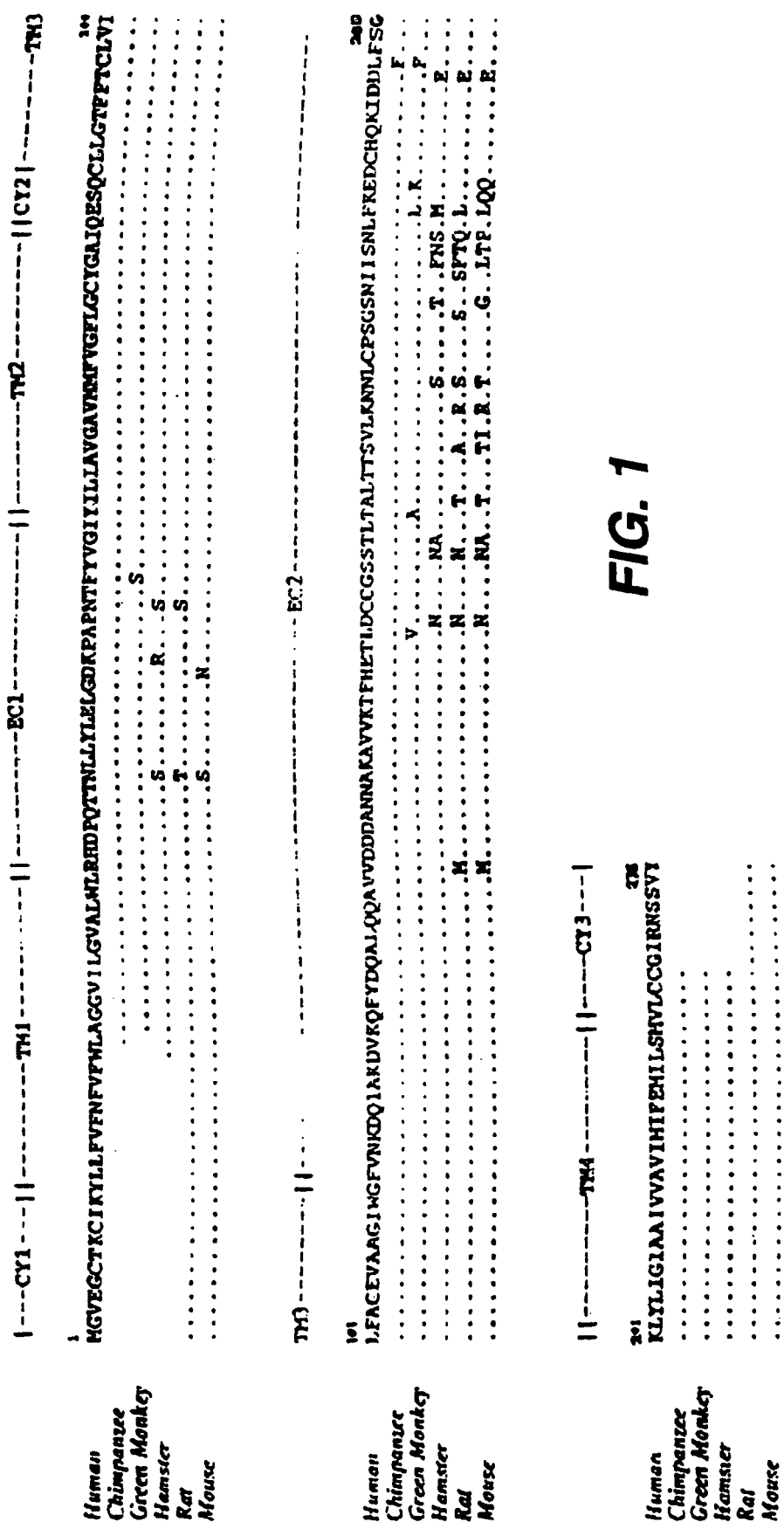
FIG. 1 is a sequence alignment showing the homology between human, chimpanzee (SEQ ID NO:16), green monkey (SEQ ID NO:17), hamster (SEQ ID NO:18), rat (SEQ ID NO:19), and mouse (SEQ ID NO:20) CD81 gene sequences.

Recombinant E2, Cell Lines, Vector DNA, and Antibodies Used in the Present Study.

The recombinant E2 used in this screening was produced in CHO cells (E2-CHO) (WO 97/09349). E2-CHO binds to the human T cell lymphoma cell line Molt-4. A subline of Molt-4 (termed A2 A6), was identified by expanding individual Molt-4 cell colonies and testing for the amount of E2-CHO that bound to the cell surface. The A2A6 subline was found to bind more E2-CHO molecule on its surface than its parental line and was therefore chosen for the source of RNA, expecting that this subline may have a higher representation of the transcript encoding the E2 binding molecule. These cells were chosen using an assay whereby human B and T lymphoma cells and hepatocarcinoma cell lines were incubated with recombinant E2 expressed in mammalian cells (CHO) as described by D. Rosa et al., *Proc. Natl. Acad. Sci. USA* 93, 1759 (1996) and stained with biotin-labelled anti-E2 antibodies as described by Rosa et al, (1996). Cells with the highest E2 binding ability were sorted using a FacsVantage (Becton Dickinson) and subcloned by limiting dilution. Growing clones were screened for E2 binding at the Facs and clones with the highest Mean Fluorescence Intensity were further expanded.

WOP is a NIH3T3-derived cell which expresses polyoma T antigen (L. Dailey and C. Basilico, *J. Virol.* 54, 739 (1985). In this cell line, plasmids containing the polyoma replication origin cari be amplified episomally. Recombinant DNA constructed with pCDM8 (Invitrogen) can be recovered from selected transfectants, which contains the polyoma replication origin and is designed for the manipulation of expression libraries in eukaryotic cells.

A mouse monoclonal anti-E2 antibody (291A2) was used for detection of E2-CHO bound on the cell surface of transfectants. This antibody was obtained as follows: BALB-c mice were immunised three times with recombinant E2 (10 μg) in complete Freund's adjuvant. Cell fusions between spleen cells and non-producing myeloma cells were made according to standard techniques. The supernatant from fusions was then screened for binding to E2 bound to Molt-4 cells, so as to identify monoclonal antibodies that bound to an exposed site on the E2 molecule. The most suitable antibody identified in this fashion was termed 291A2.

EXAMPLE 2

Construction of cDNA Library

Total RNA was extracted from the A2A6 cell line according to the method described by Chomczinsky and Sacchi (Chomczinsky, P. and Sacchi, N. (1987) *Anal. Biochem.* 162: 156–159). Poly(A)+was enriched twice using oligo(dT) cellulose. Starting from 2μg of this RNA as a template, the double strand complementary DNA was synthesized using a Superscript II cDNA synthesis kit (Life Technologies) in the presence of oligo(dT) (100 ng) and random hexamer primers (100 ng). The cDNA was blunt-ended with T4 DNA polymerase and was ligated with a BstXI linker, which allows the insertion of the fragment into the same restriction site in the polylinker region of the expression vector pCDM8. The linker-ligated cDNA was phenol-extracted and ethanol precipitated using ammonium sulphate to remove free mononucleotides, followed by Sephacryl 500 chromatography (Lifetechnologies) to size-fractionate the cDNA. The purified cDNA fragment over 500 bp were pooled and ligated with BstXI digested pCDM8 at a molecular ratio of approximately 1:1. This final ligation reaction was used from transformation of E. coli MC1061/P3 by electroporation using Gene-Pulser (BIORAD). A total of 2×10$^6$ cfu was amplified and pooled in liquid bacterial culture as a cDNA library.

EXAMPLE 3

Library Screening

The screening procedure was based largely on the method described by Campbell et al. (Campbell, I. G., Jones, T. A., Foulkes. W. D. and Trowsdale, J. Cancer Res. 51: 5329–5338, 1991). Enrichment was carried out using magnetic beads (the first to the third round) (FIG. 1A) and panning techniques (the fourth round). (FIG. 1B).

3.1 The First Round of Screening

A total of 375 μg of amplified DNA, which represents $2 \times 10^6$ of independent cDNA clones was prepared. In each transfection. 25 μg of DNA was mixed with $10^7$ WOP cells using the Gene-Pulser electroporator (BIORAD) under the conditions of 300V/500 μF. Fifteen sets of transfections were performed. After transfection, cells were incubated at 37° C. for 2 days and then the cells were detached by trypsinization and washed with PBS supplemented with 5% FCS and 0.5 mM EDTA twice by centrifugation at 360×g for 10 min at 4° C. The cell pellet was resuspended in PBS supplemented with 5% FCS and 0.5 mM EDTA ($10^7$ cells/ml) and then E2-CHO was added to the cell suspension at a concentration of 10 μg/ml. The cells were incubated on ice for 60 min. After washing twice with PBS supplemented with 5% FCS and 0.5 mM EDTA, the cell suspension was incubated with 291 A2 antibody on ice for 30 min. After washing twice with PBS supplemented with 5% FCS and 0.5 mM EDTA, 10 μl of Dynabeads (DYNAL) coupled with goat anti-mouse IG was added to the cell suspension. The mixture was gently agitated using a Coulter Mixer (Coulter) for 60 min at 4° C. Bound cells were separated using Magnetic Particle Concentrator (DYNAL) from non-binders according to the manufacturer's instructions thus enriching E2-binding transfectants. Plasmid DNA was recovered from the bound transfected cells using the protocol described by Campbell et al. (Campbell, I. G., Jones, T. A., Foulkes, W. D. and Trowsdale, J. Cancer Res. 51: 5329–5338. 1991). *E. coli* MC1061/P3 was transformed with this plasmid by electroporation. This DNA pool is referred to as the first enriched pool (1°EP).

3.2 The Second Round of Screening

A total of 150 μg of amplified DNA derived from 1°EP was prepared and 6 sets of the transfection were performed and transfectants were enriched using the same condition as in the first screening, This DNA pool is referred to as 2°EP.

3.3 The Third Round of Screening

A total of 25 μg of amplified DNA derived from 2°EP was prepared and one set of the transfection was performed. Transfectants were enriched using the same condition as in the first screening. During this separation step, transfectants formed aggregates, which might be caused by expression of irrelevant adhesion molecules. This could decrease the efficiency of enrichment because these aggregates contained magnetic beads non-specifically. To circumvent this potential problem transfectants after the second separation by Magnetic Particle Concentrator were diluted and plated on Terasaki plates. Approximately 100 of single cells identified under microscope were pooled and plasmid DNA was extracted from them. The DNA pool prepared from this step is referred to as 3°EP.

3.4 The Fourth Round of Screening

291A1 monoclonal antibody was incubated in a Petri dish (90 mm) at a concentration of 1 Olg/ml overnight at 4° C. A total of 25 μg of amplified DNA derived from 3°EP was prepared and one set of transfections was performed. The transfected cells were incubated with E2-CHO as described above, and placed onto the 291A2-coated plates for 60 min at 4° C. After rinsing with a large excess of PBS supplemented with 5% FCS and 0.5 mM EDTA twice, the bound cells were directly treated with the lysing solution and plasmids were extracted as described as before. This DNA pool is referred to as 4°EP.

3.4 Identification of cDNA Encoding a Molecule Binding to the Recombinant E2

Figure 2B:
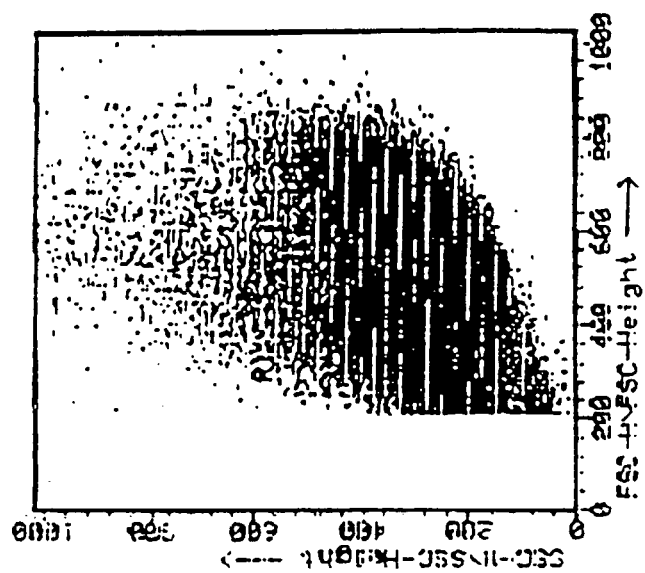
FIG. 2 is a FACS scan analysis of E2 bound ceus.
Figure 2A:
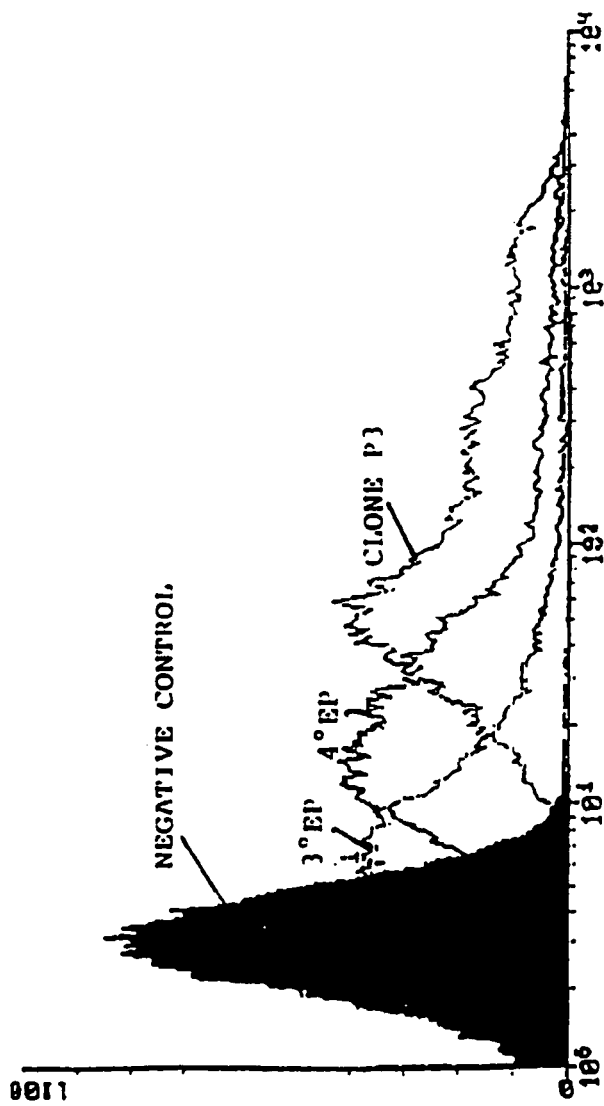

DNA was isolated from single colonies derived from 4°EP. A single transfection was performed for each plasmid preparation using the same conditions as used for the previous screening steps. E2-binding of the transformants was detected using a phycoerythrin-conjugated monoclonal Fab fragment of goat anti-mouse Ig instead of the antibody-coupled Dynabeads. Transfectants of 3°EP and 4°EP were also analyzed in the same way. The E2-bound cells were detected on FACScan (Becton Dickinson) and analyzed with LYSIS II program (Becton Dickinson) (FIG. 2). E2-CHO binds increasingly as the purification step advances. A single clone P3 showed strong E2-binding.

EXAMPLE 4

DNA Sequencing Determination and Analysis

P3 contains a insert of approximately 1 kb. The DNA sequence of the insert of the cDNA clone which confers E2-binding to WOP upon transfection was determined by an automated sequencing system using the T7 primer, whose sequence is located adjacent the cloning site of pCDM8. The sequence was screened through the GenBank databases using the GCG programs on a UNIX computer. This analysis revealed that the 5' part of P3 insert is identical to human CD81 (TAPA-1). Restriction analysis of P3 using three enzymes (BstXI, HincII and NcoI) also agreed with the restriction map of human CD81 cDNA.

EXAMPLE 5

Binding of CD81 to Recombinant E2

Figure 3:
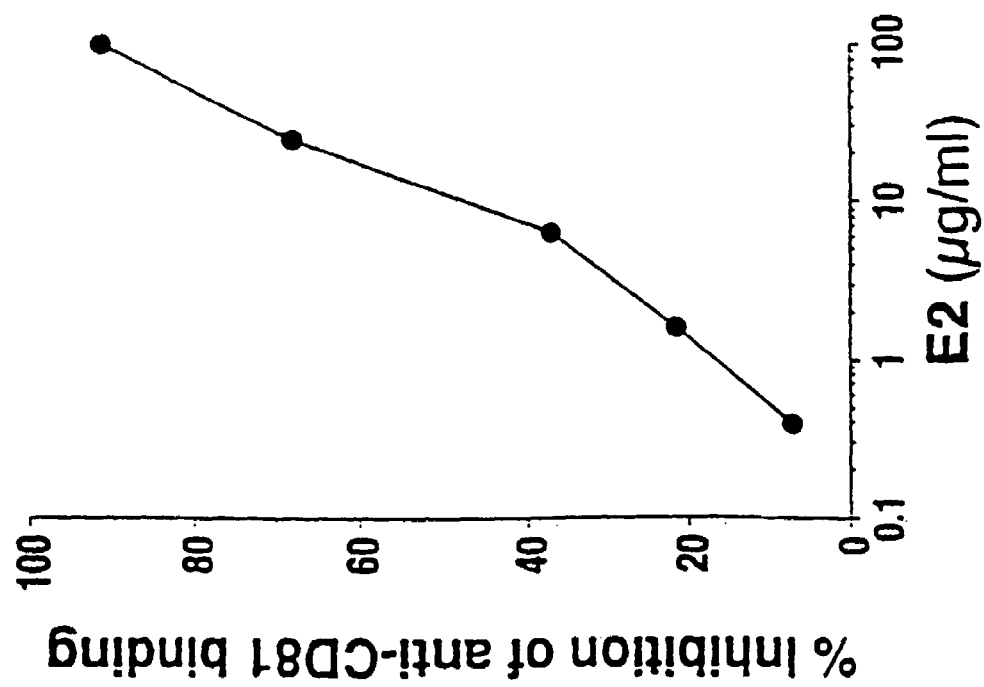
FIG. 3 shows the dose-dependent inhibition of anti-CD81 binding to B cells by recombinant E2. The data are expressed as % inhibition of mean fluorescence intensity.

Anti-CD81 antibodies were used to assess the interaction between E2 and CD81. EBV-B cells were incubated with increasing concentrations of recombinant E2 for 1 hour at 4° C. and then stained with an anti-CD81 monoclonal antibody (clone JS-81, Pharmingen). As shown in FIG. 3, recombinant E2 was found to competitively inhibit the binding of anti-CD81 antibodies to EBV transformed B-cell lines (EBV-B cells). The data are expressed as % inhibition of mean fluorescence intensity (Rosa et al. 1996).

Figure 4:
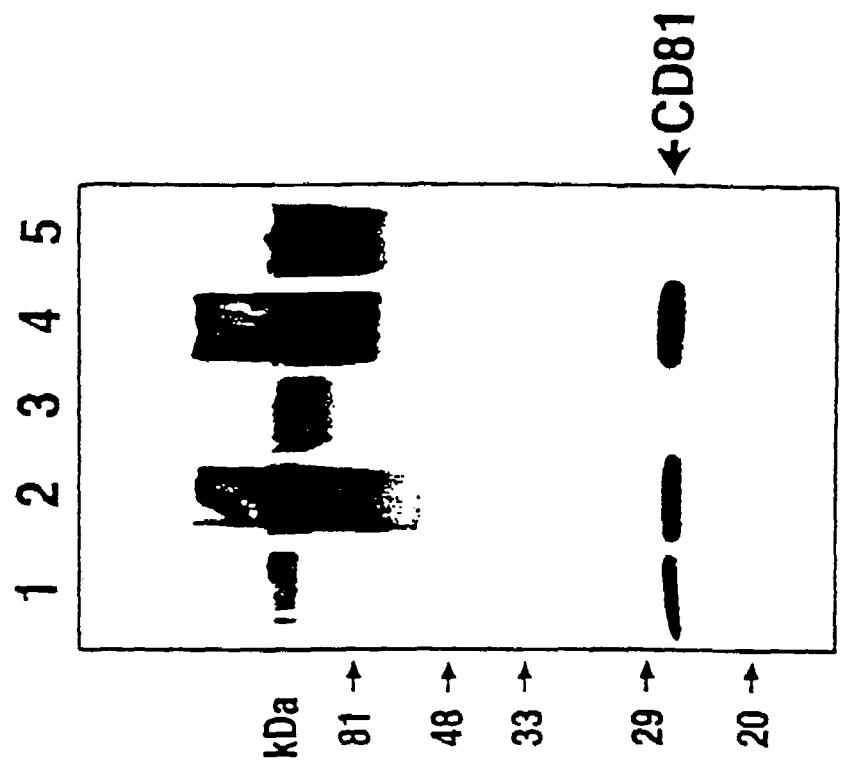
FIG. 4 is an immunoblot showing the recognition of the membrane protein faction immunoprecipitated by anti-CD81 antibody. Lane 2: recombinant E2 precipitated with chimpanzee antiserum to E2; lane 3, recombinant E2 precipitated with chimpanzee pre-immune serum lane 4: 20 μg of anti-CD81 mAb (clone JS81 Pharmingen) precipitated with goat anti-mouse IgG, lane 5: control, (20 μg of an irrelevant monoclonal antibody, anti-human CD9, ATCC) precipitated with goat anti-mouse IgG linked to protein A sepharose. Lane 1: positive control, membrane protein preparation.

In addition, E2 reacts in Western blot with anti-CD81 precipitated material (FIG. 4). This Figure shows E2 recognition of membrane protein fraction immunoprecipitated by anti-CD81 antibody. Approximately 300 μg of membrane protein extract prepared from the A2A6 cell line were solubilised in 8 mM CHAPS in PBS pH 7.4, incubated with 10 μg recombinant E2 (lanes 2 and 3), with 20 μg of anti-CD81 mAb (clone JS81; Pharmingen) (lane 4), or as control, with 20 μg of an irrelevant monoclonal antibody (anti-human CD9, ATCC) (lane 5) for 2 hours at 4° C., and finally precipitated with chimpanzee antiserum to E2 (lane 2), chimpanzee pre-immune serum (lane 3), or goat anti-mouse IgG (lanes 4 and 5) bound to protein A sepharose (CLAB, Pharmacia). The pellet was dissolved in Laemmli buffer and subjected to SDS-PAGE under non-reducing conditions. After electroblotting, the PVDF membrane (Millipore) was incubated overnight with 1 µg/ml of recombinant E2 at room temperature and for 2 hours with 291A2 anti-E2 monoclonal antibody. E2 binding to immunoprecipitated proteins was detected with an anti-mouse IgG peroxidase-conjugated polyclonal antibody (Amersham). As a positive control membrane proteins also were loaded on the gels (lane 1). The mobility of molecular weight standards is indicated on the left in kilodaltons.

CD81 is also expressed on fresh lymphocytes and hepatocytes as demonstrated by immunohistochemical staining with biotin-labelled-E2 or anti-CD81 (data not shown).

To assess whether CD81 could mediate the internalisation of ligands we exploited the fact that CD81 forms a complex with CD19 and CD21 on the surface of B lymphocytes (D. T. Fearon and R. H. Carter, 1995, *Annu. Rev. Immunol.* 13, 127). B cells were incubated with E2 at 37° C. for different times, after which CD19 or CD21 levels on the cell surface were measured by immunofluorescence. Incubation of B cells with E2 resulted in down-regulation of both CD19 and CD21 (data not shown). It thus seems as if CD81 is able to mediate the internalisation of both these ligands.

EXAMPLE 6

The Major Extracellular Loop of CD81 Binds Recombinant E2 and Viral Particles.

To map the CD81 domain that binds E2 protein our efforts were focused on the EC2 hydrophilic extracellular loop of the protein. This fragment was expressed in *E. coli* as a Thioredoxin-EC2 fusion protein that has an enterokinase site between thioredoxin and EC2, and as a GST-EC2 fusion protein which has a thrombin site between GST and EC2 and a hexa-histidine tag added to the carboxyl-terminus of the protein. We show that both proteins are expressed and are able to bind HCV E2. In competition experiments we also show that the purified fusion proteins and the EC2-His fragment excised from GST-thrombin-EC2-(His)$_6$ are able to inhibit the binding of E2 on the surface of CD81 expressing cells.

6.1 Cloning of EC2 in pThio-His.

Figure 5:
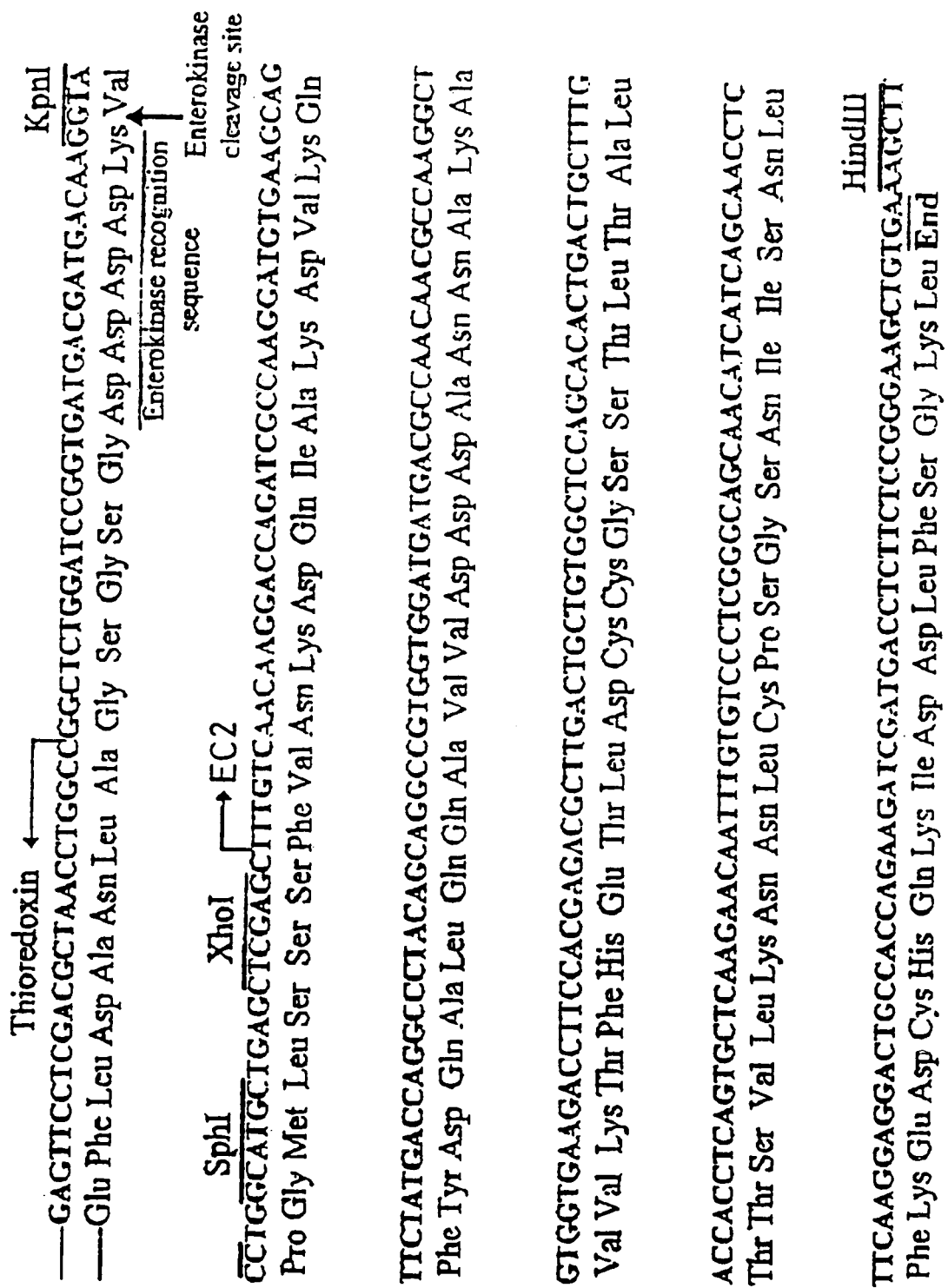
FIG. 5 shows the nucleotide and deduced amino acid sequences (SEQ ID NOS:12 & 13) of the EC2 fragment cloned in pThio-His C and the upstream plasmid sequence coding for the carboxyl terminus of thioredoxin and for the enterokinase cleavage site.

FIG. 5 shows the nucleotide and the deduced amino acid sequences of the EC2 fragment cloned in pThio-His C and the upstream plasmid sequence coding for the carboxyl terminus of thioredoxin and for the enterokinase cleavage site. As shown, EC2 is fused in frame with: thioredoxin through the enterokinase site which can be exploited to remove thioredoxin from the fusion protein.

The fragment coding for EC2 was PCR-amplified from the plasmid pCDM8/P3 using the following oligodeoxynucleotides.

Using standard cloning techniques (Sambrook et al., 1989) the PCR product was double-digested with XhoI and HindIII, ligated to pThio-His C (Invitrogen) digested with the same restriction enzymes, and transformed into Top10 *E. coli* cells. After selection of the transformants by restriction enzyme analysis and DNA sequencing of the plasmids, a correct construct coding for the expected thioredoxinenterokinase site-EC2 fusion protein was identified. Glycerol batches of selected clones were stored to −80° C.

Figure 6:
FIG. 6 shows the appearance of a protein band of the expected molecular mass for thioredoxin-EC2 in the extract from the induced sample.

Total protein extracts of the thioredoxin-EC2 expressing clone before and after IPTG addition were subjected to SDS-PAGE to analyse protein expression. FIG. 6 clearly shows the appearance of a protein band of the expected molecular mass (23.4 kDa) in the extract from the induced sample. The figure also shows the reactivity of the fusion protein with E2. The TOP10 *E. coli* clone containing the pThio-his C-EC2 plasmid and a TOP10 clone containing the pThio-H is C plasmid devoid of insert were induced, soluble protein extracts were prepared from both clones and subjected to Far Western Blot with E2 protein. For this blot, protein samples were brought to 1×loading sample buffer (LSB) (5% w/v SDS, 10% v/v glycerol, 62.5 mM Tris-HCl, 0.05% Bromophenol Blue) using a 3×LSB solution. The samples were run onto a 15% polyacrylamide gel and transferred to a PVDF membrane (Immobilon-P, Millipore). The membrane was incubated for 30 min in blocking solution (PBS, 10% w/v non-fat dried milk, 0.05% v/v Tween 20). Following an incubation of 15 hours at 4° C. with blocking solution containing 1 µg/ml of CHO-E2, the membranes were incubated for 2 hours with the 291A2 anti-E2 monoclonal antibody diluted 1:250, and for 1 hour with a peroxidated goat antimouse Ig antibody (Sigma) diluted 1:2000. Three washing steps between all incubation steps were performed using blocking solution, which was also used to dilute the antibodies. After a final wash with PBS the membranes were incubated for 1 min with luminol (ECL, Amersham) and exposed on Hyper-film (Amersham).

As can be seen from these Figures, a band corresponding to the molecular weight of Thioredoxin-EC2 was visible in the lane where the soluble proteins from the pThio-H His C-EC2 were loaded. Such a band was absent in the lane where the soluble proteins of the pThio-H is C clone were loaded.

6.2 Purification of Thioredoxin-EC2

For the purification of thioredoxin-EC2 the following procedure was developed:

1) osmotic shock of the cells, 2) protein precipitation with 30% saturation ammonium sulphate, and 3) IMAC. After osmotic shock about 50% of the fusion protein was released from the cells together with contaminant proteins. The ammonium sulphate precipitation resulted in a pellet which contained thioredoxin-EC2 devoid of the bulk of contaminant proteins. IMAC of the resuspended precipitate resulted

```
     Forward BL                      EC2
5'GGCGGGGGTGGATCCGGGGGTGGAGGCTCGAGCTTTGTCAACAAGGACC3'        (SEQ ID NO:1)

XhoI   Phe Val Asn Lys Asp          (SEQ ID NO:2)

Reverse BL    EC2

5'CCCCAAGCTT TCA CAG CTT CCC GGA GAA GAG GTC ATC G3'         (SEQ ID NO:3)

HindIII Stop Leu Lys Gly Ser Phe Leu Asp Asp         (SEQ ID NO:4)
``` in a fusion protein which was about 85% pure as assessed by SDS-PAGE. With this procedure we purified 5 mg thioredoxin-EC2 from a liter of culture. This procedure is set out in detail below.

The *E. coli* clone expressing Thioredoxin-EC2 was inoculated in 500 ml LB medium containing 100 µg/ml ampicillin. At $OD_{600}$=0.5, 0.5 mM IPTG was added to the culture and growth was continued at 37° C. for additional 3.5 hours. The culture was then centrifuged at 4000×g for 10 min at 4° C., the cell pellet was resuspended with 50 ml ice cold hypertonic solution (20 mM Tris-HCl, 2.5 mM EDTA, 20% sucrose, pH 8) and left on ice for 10 min. The resuspended cells were centrifuged again as above and the pellet was resuspended in hypotonic buffer (20 mM Tris-HCl, 2.5 mM EDTA, pH 8) to osmotically shock the cells. After 20 min at 0° C. the suspension was centrifuged at 12.000×g for 10 min at 4° C., the supernatant was brought to 30% $NH_2(SO_4)_2$ using a room temperature saturated solution of the salt. The suspension was incubated overnight at 4° C. and then centrifuged at 10.000×g for 10 min. The pellet was resuspended using 15 ml of 20 mM Phosphate buffer, 500 mM NaCl, pH 6, clarified by centrifugation, and loaded on a 2 ml column of Nickel activated Chelating Sepharose Fast Flow (Pharmacia) equilibrated in the same buffer.

After adsorption, the column was washed with 10 ml of the equilibrium buffer (flow rate 0.5 ml/min), and then the Thioredoxin-EC2 was eluted using a 30 ml gradient 0–50 mM Imidazole in 20 mM Phosphate buffer, 500 mM NaCl, pH 6 followed by an isocratic elution with 10 ml of 400 mM imidazole. 2.4 ml fractions were collected. The fractions containing the recombinant protein were pooled, dialysed against PBS, and stored to −20° C. Proteins were analysed by means of SDS-PAGE and protein content was assayed by the Bradford method using BSA as a protein standard.

Figure 7:
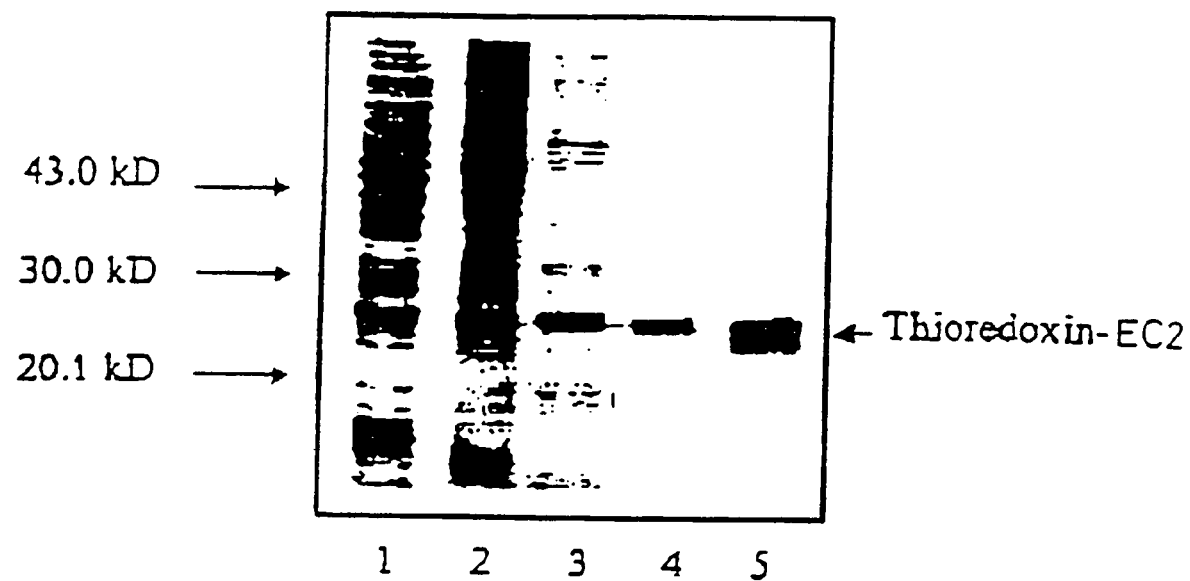
FIG. 7 is a Coomassie Blue stained gel showing the purification of thioredoxin-EC2.

Purified Thioredoxin-EC2 is shown in FIG. 7.

6.3 Cloning of EC2-(HiS)$_6$ in VGEX-KG

Figure 8:
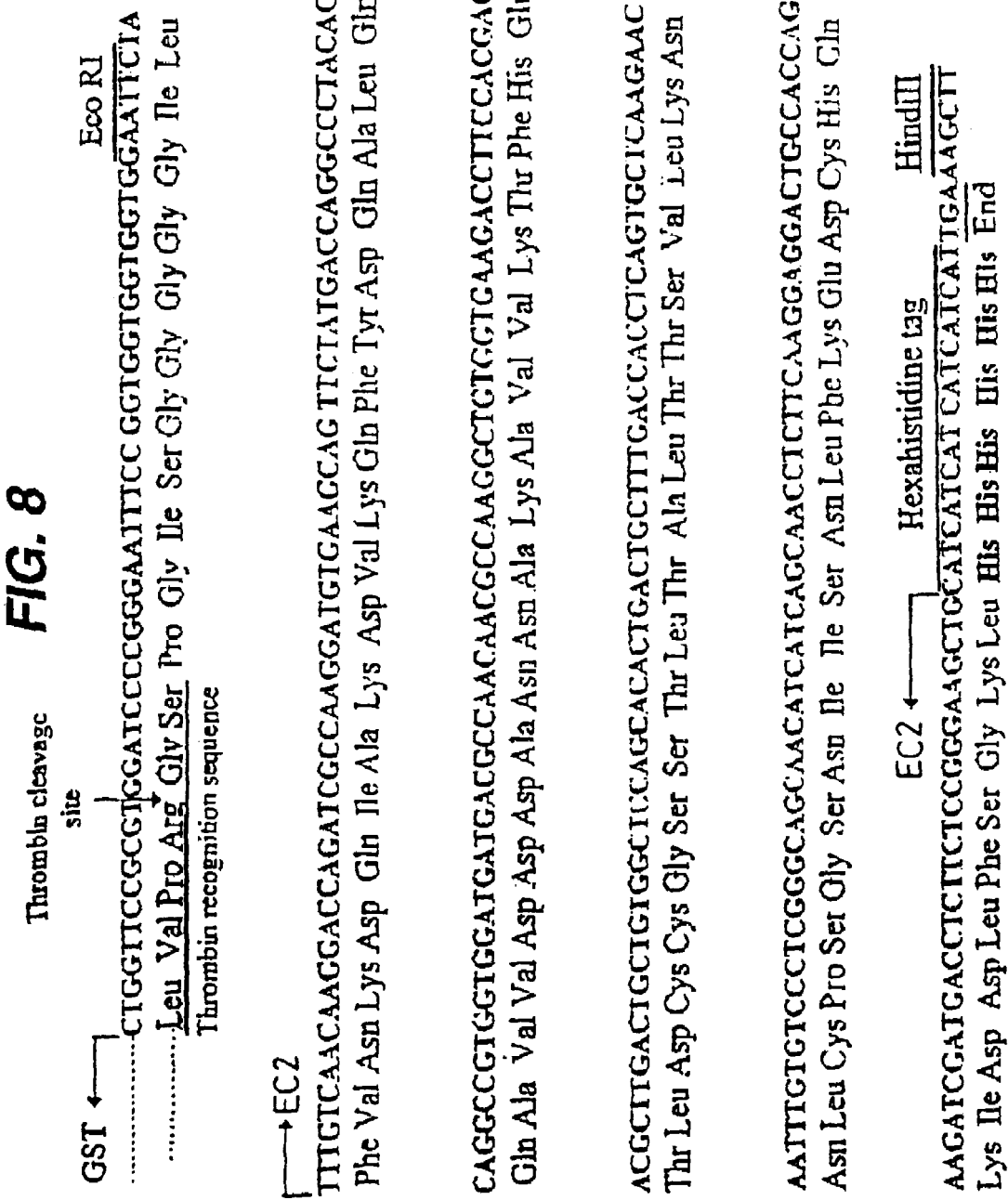
FIG. 8 represents the nucleotide and deduced amino acid sequence (SEQ ID NOS: 14 & 15) of the EC2-HiS6 fragment cloned into pGEX-KG as well as the upstream plasmid sequence coding for the carboxyl terminus of GST, the thrombin cleavage site and a small glycine spacer.

FIG. 8 represents the nucleotide and deduced amino acid sequence of the EC2-(His)$_6$ fragment cloned in pGEX-KG as well as the upstream plasmid sequence coding for the carboxyl terminus of GST, the thrombin cleavage site, and a small glycine spacer. As shown, EC2 is fused in frame with GST through the thrombin site, which can be exploited to remove GST from the fusion protein. The glycine-rich spacer, located between thrombin site and EC2, facilitates the cleavage of the fusion protein by thrombin (Guan, K. L. and Dixon, J. E. (1991) *Anal. Biochem.* 192, 262–267).

The fragment coding for EC2 was PCR-amplified from the plasmid pCDM8/P3 using the following oligodeoxynucleotides.

The PCR product was digested with XhoI and HindIII, ligated to pGEX-KG (Guan, K. L., and Dixon, J. E. (1991) *Anal. Biochem.* 192, 262–267) digested with the same restriction enzymes, and transformed into TOP10 *E. coli* cells. After selection of the transformants by restriction enzyme analysis and nucleotide sequencing of the plasmids, a plasmid having the expected size of the insert was found to have also the correct EC2-(His)$_6$ sequence in frame with the upstream thrombin and GST coding sequence. The plasmid prepared from the selected TOP10 clone was then transformed into BL21 cells. Glycerol batches of selected clones were stored to −80° C.

Figure 9:
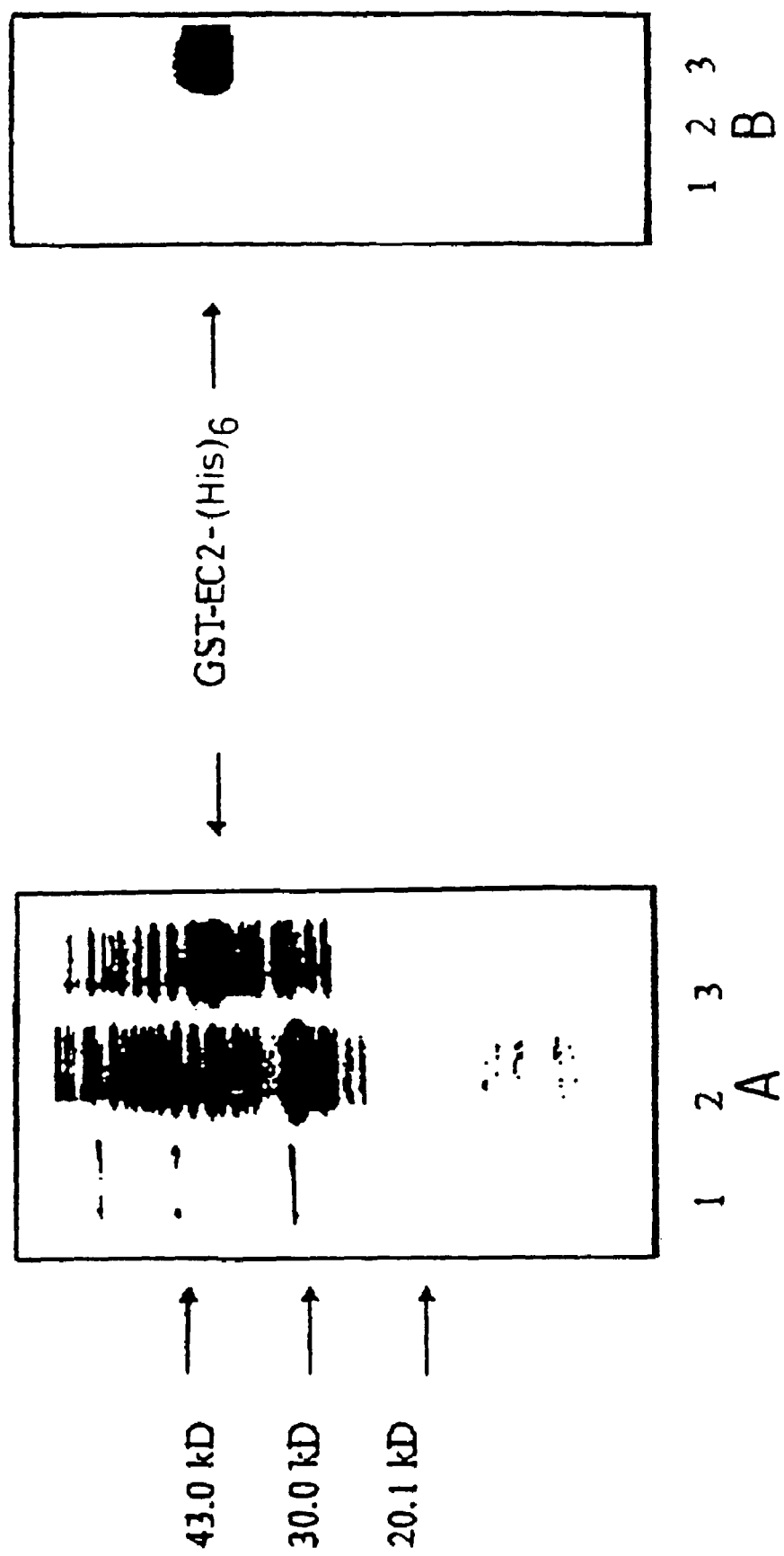
FIG. 9 represents an SDS-PAGE of total proteins of the TOP10 E. coli clone which express GST-EC2-(His)$_6$.

FIG. 9 represents an SDS-PAGE of total proteins of the TOP10 *E. coli* clone which expresses GST-EC2-(His)$_6$. This analysis clearly shows that in the extract of the induced sample a protein band with the expected molecular mass (39 kDa) was present. The corresponding Far Western Blot clearly shows the E2 specifically reacts with the fusion protein.

6.4 Purification of GST-EC2-(His)$_6$

Figure 10:
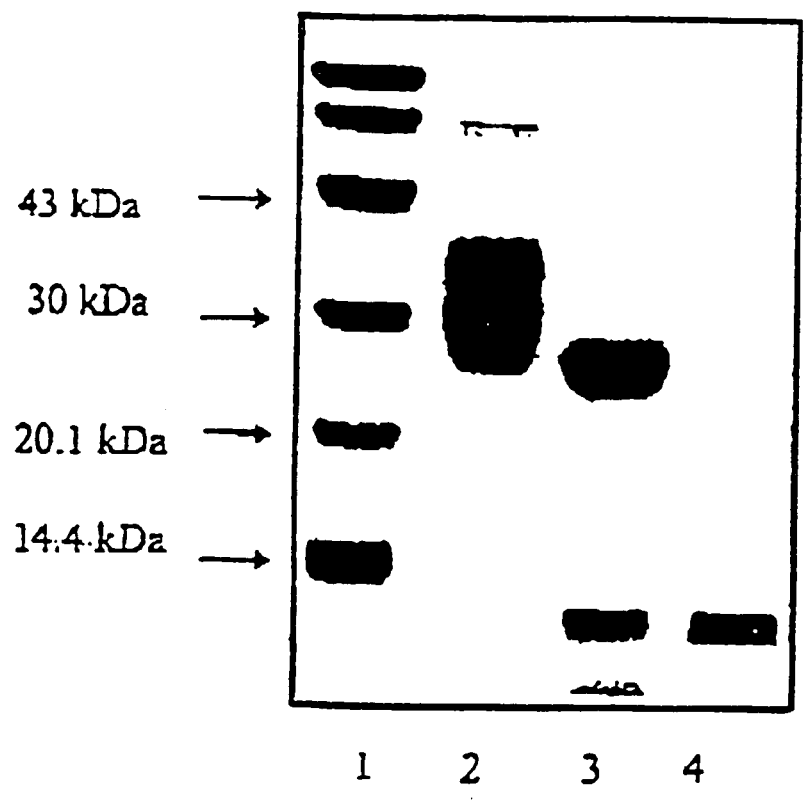
FIG. 10 is a Coomassie-stained SDS-PAGE showing thrombin cleavage of GST-EC2-(His)$_6$ after purification of the protein on a glutathione sepharose column.

The GST-EC2-(His)$_6$ fusion protein was purified on a glutathione sepharose column and digested with thrombin (FIG. 10). After digestion, the EC2-(His)$_6$ moiety was further purified by two additional chromatographic steps consisting of a glutathione sepharose column to remove the GST fragment and IMAC chromatography. This procedure is detailed below.

A single colony of an *E. coli* clone expressing the GST-EC2 fusion protein was inoculated in 10 ml LB, 100 µg/ml Amp and cells were grown overnight at 37° C. The culture was then inoculated in 500 ml of medium and when $OD_{600}$=0.5 was reached 0.5 mM IPTG was added. After 3.5 hours the cells were harvested by centrifugation, resuspended with 9 ml PBS and disrupted with two passages at 18.000 psi using a French Press (SLM Aminco). The lysate was centrifuged at 30.000×g and the supernatant was loaded on a column of 1 ml of Glutathione Sepharose 4B (Pharmacia) equilibrated in PBS.

The column was washed with 10 ml PBS, and eluted with 4 ml of 50 mM Tris-HCl, 10 mM reduced glutathione, pH 8. The eluted proteins were dialysed against PBS and stored to −20° C.

6.5 Digestion of GST-EC2-(His)$_t$ with Thrombin and Purification of EC2-(His)$_6$ 9.6 mg of protein recovered from the glutathione sepharose column were digested with 22 units of thrombin (Pharmacia) for 8 hours at room temperature, then the enzyme was inactivated using 0.13 mM PMSF (Sigma). The reaction mixture was then dialysed against PBS and loaded

```
      EC2 Forward    EC2
5'CAAAAGGAATTCTA TTT GTC AAC AAG GAC CAG ATC GCC AAG3'       (SEQ ID NO:5)
        EcoRI   Phe Val Asn Lys Asp Gln Ile Ala Lys          (SEQ ID NO:6)

Reverse BLH    His tag      EC2
5'CCCCAAGCTTTCAATGATG ATG ATG ATG ATG CAG CTT CCC GGA        (SEQ ID NO:7)
GAAG3'
      HindIII Stop His His His His His His Leu Lys Gly Ser   (SEQ ID NO:8)
Phe.
``` into 0.5 ml of GST-sepharose column equilibrated in PBS. The column was washed with 1 ml of PBS. The flow-through and the wash were pooled and loaded into 0.250 ml of Nickel-activated chelating sepharose column. EC24(His)$_6$ was recovered from the column eluting with 1 ml of 20 mM phosphate buffer, 500 mM NaCl, 400 mM imidazole, pH 7.8. A dialysis was then performed against PBS.

EXAMPLE 7

Binding of CD81 Fragment to Virus

Figure 11:
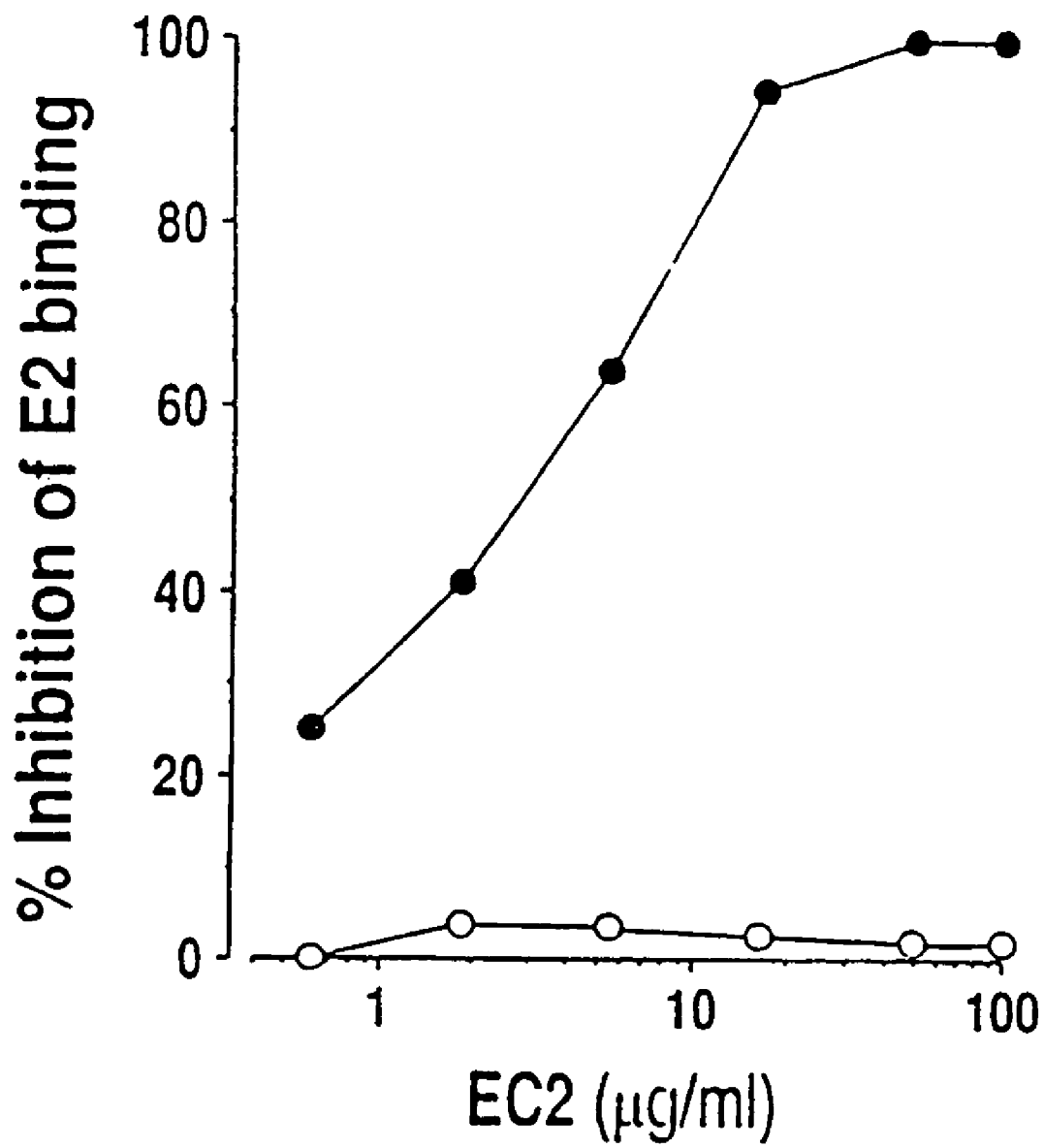
FIG. 11 shows the dose-dependent inhibition of E2 binding to hepatocarcinoma cells by recombinant molecule expressing the major extracellular loop (EC) of human CD81.

The proteins containing the human, but not the mouse EC2 loop of CD81, bound to E2 in western blot (data not shown) and inhibited binding of E2 to human cells (FIG. 11).

The chimeric proteins were coated on polystyrene beads and incubated with an infectious plasma containing known amounts of viral RNA molecules. After washing, the bead-associated virus was assessed by quantitative RT-PCR for the amount of bound HCV RNA. This experiment was performed as set out below.

Polystyrene beads (¼ inch diameter) (Pierce) were coated overnight with purified EC2 recombinant protein in citrate buffer pH4 at room temperature. After saturation for one hour with 2% BSA in 50 mM TrisCl pH 8, 1 mM EDTA. 100 mM NaCl (TEN) buffer, each bead was incubated at 37° C. for 2 hours in 200 µl TEN-diluted infectious chimp plasma containing $5 \times 10^5$ HCV RNA molecules.

For inhibition experiments, the EC2-coated polystyrene beads were incubated with 10µg/ml of purified monoclonal antibodies for one hour at room temperature before incubation with the virus. Each bead was washed 5 times with 15ml TEN buffer in an automated washer (Abbot) and viral RNA was extracted using the Viral Extraction Kit (Qiagen). RNA (8 ml) was reverse-transcribed at 42°C. for 90 minutes in 20 ml Buffer A (Perkin Elmer Taq Man) containing 100pmol of the HCV antisense primer CGGTTCCGCAGACCACTATG (SEQ ID NO: 9), 40 U RNAsin (Promega), 5 nmol dNTPs, 110 nmol MgC12, IOU M-MuRT (Bohennger). cDNA (20 ml) was amplified using a PerkinlElmer ABI 7700 Sequence Detection System (45 cycles) in 50 ml Buffer A containing 100 pmol of the HCV sense primer TCTTCACGCA-GAAAGCGTCTA (SEQ ID NO:10), 5 pmol of the fluorescent detection probe 5'(FAM)TGAGTGTCGTGCAGC-CTCCAGGA(TAMRA) (SEQ ID NO:11) (kindly provided by David Slade, Pharmacia and Upjohn), 15 nmol dNTPs, MgC1$_2$ and 1.25U Taq Gold (Perkin-Elmer, Foster City, CA). All reactions were quantified using HCV (genotype la) infected plasma (bDNA titer of 30 mEq/ml) to generate a standard curve. Sequence Detector Software from Perkin-Elmer has been previously described (U. E. Gibson, C. A. Heid and P. M. Williams, Genome Res. 6. 995 (1996)).

Figure 12:
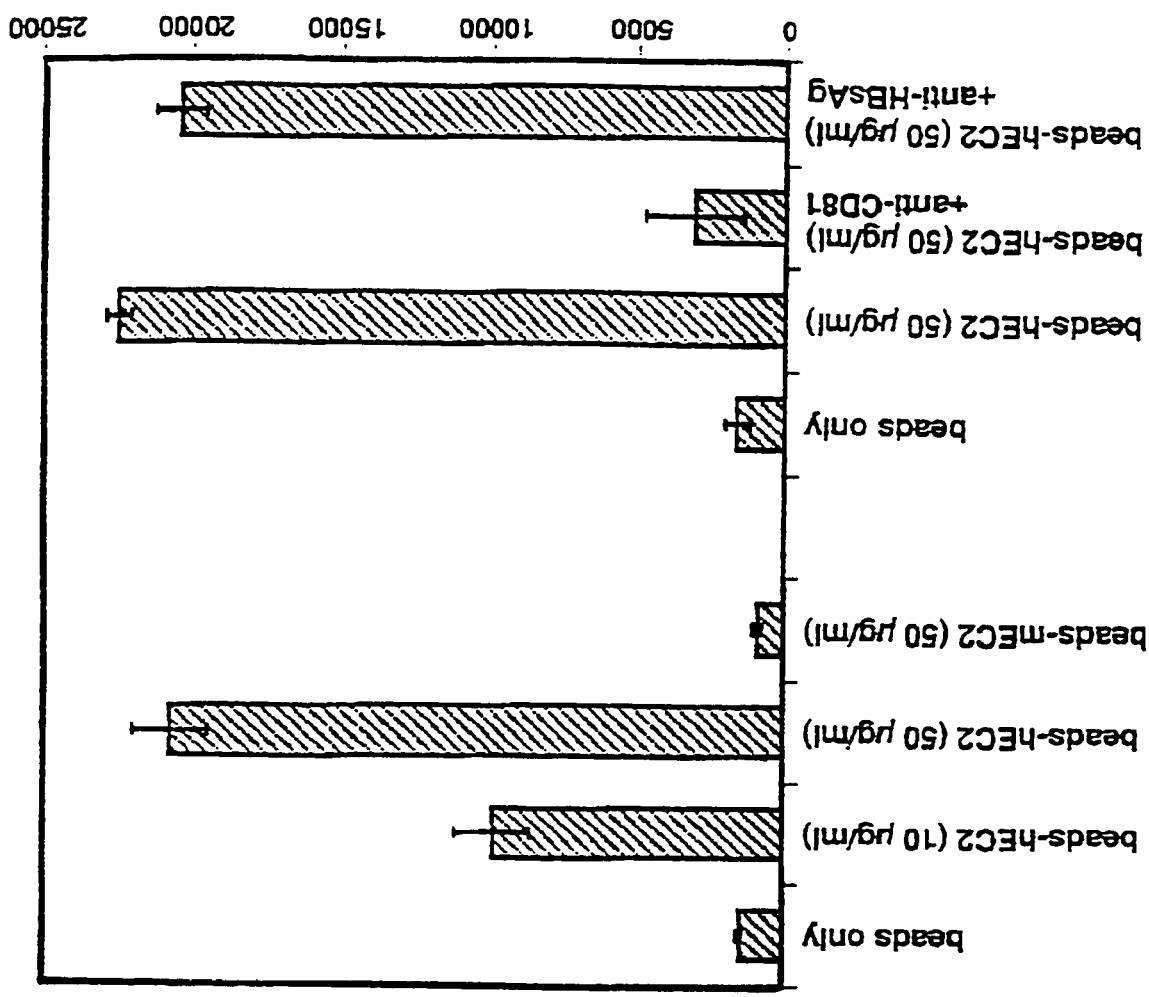
FIG. 12 shows binding of HCV to CD81.

As shown in FIG. 12, the molecules containing the human CD81 extracellular loop bound HCV in a concentration-dependent fashion, and pre-incubation of the chimeric proteins with anti-CD81 antibodies inhibited virus binding. Furthermore, serum from chimpanzees which were protected from homologous challenge by vaccination with recombinant E1/E2 envelope heterodimer (Q.-L. Choo et al. Proc. Natl. Acad. Sci. USA 91. 1294 (1994)) completely inhibited HCV binding to bead-coated-CD81, while serum from vaccinated and non-protected animals did not (data not shown).

These data demonstrate that expression of human CD81, and in particular its major extracellular loop are sufficient for binding not only E2 but also HCV particles. Given the wide distribution of CD81 (S. Levy, S. C. Todd and H. T. Maecker, Annu. Rev. Immunol. 16, 89 (1998), these results imply that HCV binds and may be internalised by a variety of cells other than hepatocytes. Indeed, HCV RNA has been found in T and B lymphocytes and monocytes (K. Blight, R. R Lesniewski, J. T. LaBrooy and E. J. Gowans, Hepatology 20, 553 (1994); P. Bouffard et al., J. Infect. Dis. 166, 1276 (1992); Zignego et al., J. Hepatol. 15, 382 (1992)). Whether virus binding is followed by entry and infection in all cell types is not clear because of the lack of an efficient HCV culture system in vitro. It may well be that CD81 is an HCV attachment receptor and that additional factors are required for viral fusion or infectivity.

CD81 participates in different molecular complexes on different cell types, a fact that may influence its capacity to serve as a receptor for HCV infection or to deliver regulatory signals to target cells. For instance, it associates with integrins on epithelial and hematopoietic cells (F. Berditchevski, M. Zutter and M. E. Hemler, Mol. Biol. Cell 7, 193 (1996); B. A. Mannion, F. Berditchevski, S.-K. Kraeft, L. B. Chen and M. E. Hemler, J. Immunol. 157, 2039 (1996)), whereas it is part of a signaling complex containing CD21, CD19 and Leu13 on B cells (L. E. Bradbury, G. S. Kansas, S. Levy, R. L. Evans and T. F. Tedder. J. Immunol. 149, 2841 (1991)). This complex has been shown to facilitate antigen specific stimulation by lowering the activation threshold of B cells (D. T. Fearon and R. H. Carter, Annu. Rev. Immunol. 13, 127 (1995)). It is worth noting that HCV appears to use a molecule that is part of the same complex containing the EBV receptor (CD21) (N. R. Cooper, M. D. Moore and G. R. Nemerow, Annu. Rev. Immunol. 6, 85 (1988)), and the ability of EBV to activate and immortalise B lymphocytes is well documented.

EXAMPLE 8

Construction of Transgenes

The following constructs were designed and made in order to generate mice transgenic for human CD81.

1. Addition of Splicing and Polyadenylation Signals of Rabbit Beta-globin Gene to the Human CD81 cDNA Fragment The human CD81 cDNA fragment from the pCDM8/P3 clone was transferred into a pBluescript KS II(+) vector (Stratagene) and was then inserted into the pSPP plasmid (derived from BMGSC expression vector, a kind gift from Dr. Karasuyama, Basel Institute for Immunology) between two fragments, one containing the second intron and the other containing the polyadenylation signal of the rabbit beta-globin gene (position 902–1547 and 1543–2081, respectively, GenBank accession No. M12603) (PSR1P in FIG. 11). The resulting recombinant DNA fragment was excised from the pBluescript KSII(+) vector (Stratagene) by SalI (at 5' end) and BamHI (at 3' end).

2. Creation of a Transgene for Ubiquitous Expression of Human CD81

The SalI-BamHI fragment of the pSRIP insert was inserted into the compatible restriction sites of pCAGmcs, a modified plasmid of pCAGGS (a kind gift from Dr. J. Miyazaki at Osaka University, Japan, under restricted permission), which contains chicken beta-actin promoter and human cytomegalovirus enhancer (Niwa, H. et al., Gene 108, p193 (1991). (pCAGSR1Pp in FIG. 12). The 3.8 kb EcORI-BamHI fragment was submitted to zygote injection.

3. Creation of a Transgene for Liver-specific Expression of Human CD81

Figure 13:
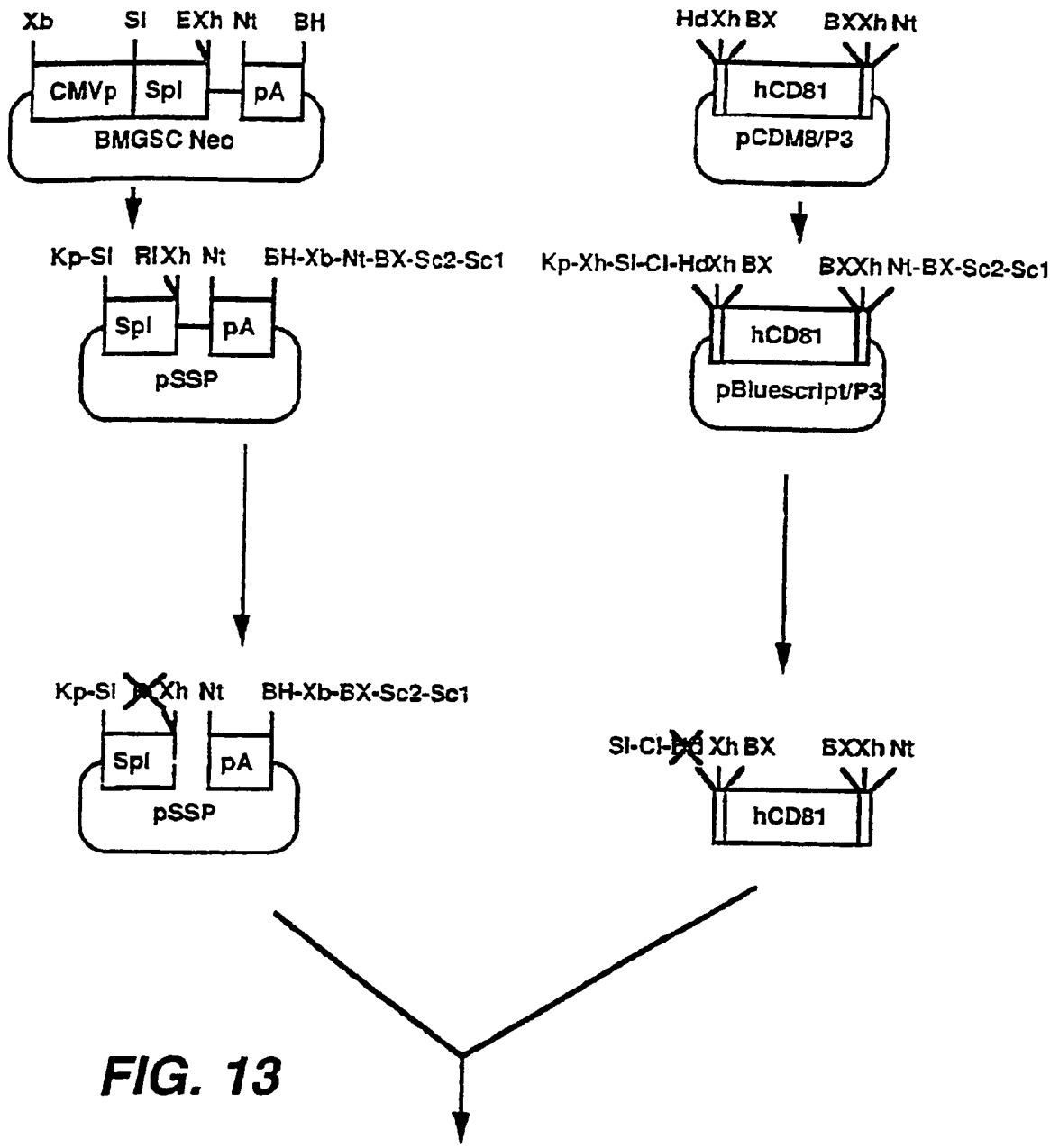
FIGS. 13–17 show the construction of nucleic acid vectors for use in the generation of mire transgenic for the human CD81 gene.
Figure 13:
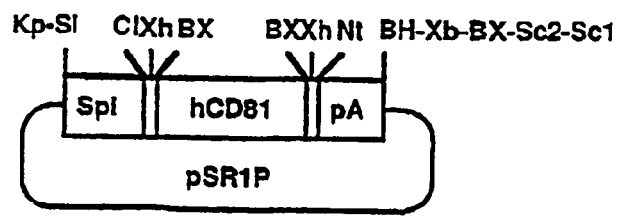
Figure 14:
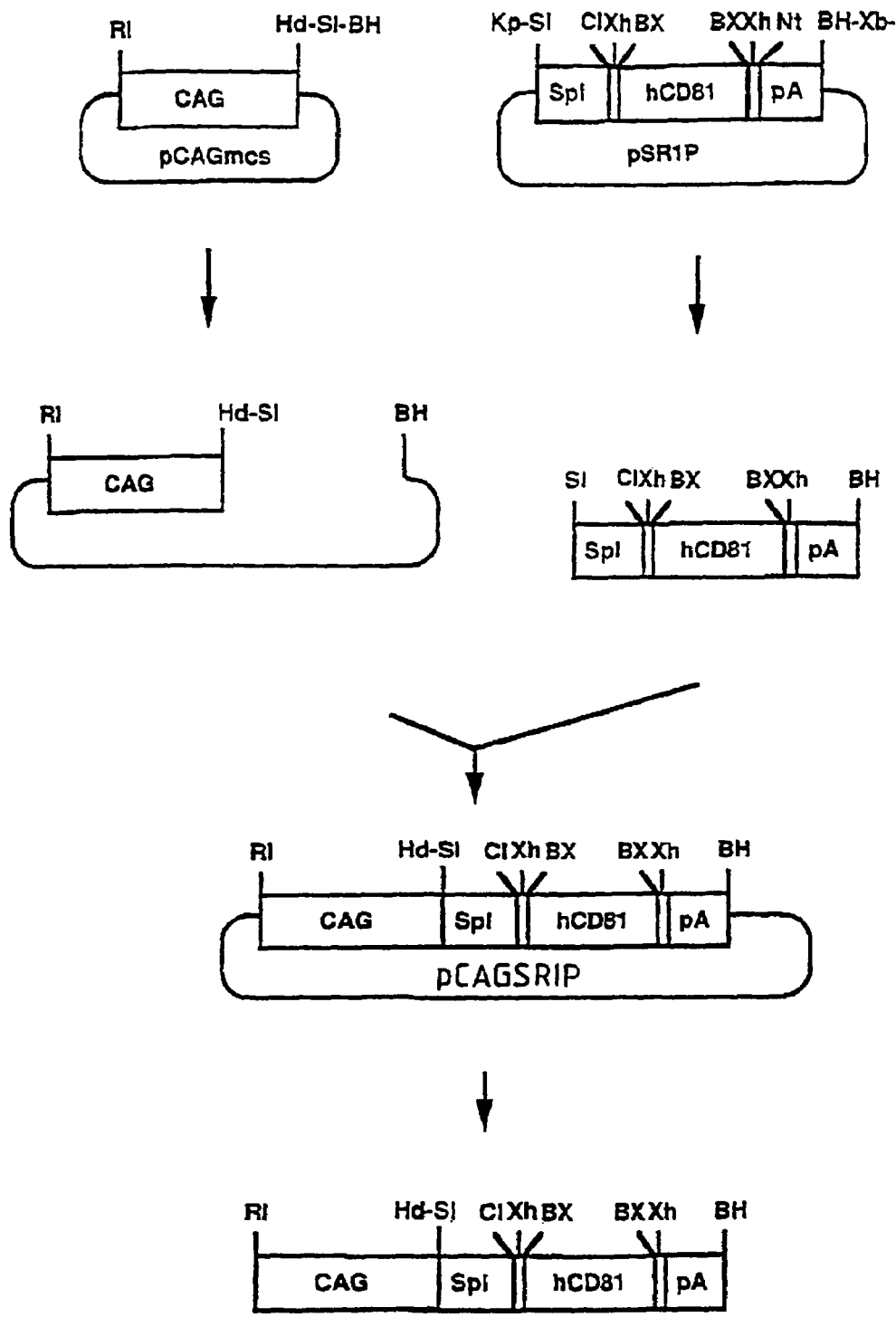

The SalI site of pSR1P was converted to a BamHI site by BamHI linker ligation after blunt-end formation with Klenow fragment of *E. coli* DNA polymerase 1. This BamHI fragment was inserted into the BamHI site of the ALB e/p plasmid, carrying the mouse albumin promoter and enhancer (Pinkert, C. A. et al., Genes Dev. 1, p268 (1987) (received from Dr. F. Chisari, Scripps Research Institute. La Jolla, San Diego). (pAIbSRIP in FIG. 13) The 4.5 kb NotI-EcORV fragment was submitted to zygote injection.

4. Creation of a Transgene for B Lymphocyte-specific Expression of Human CD81

Figure 15:
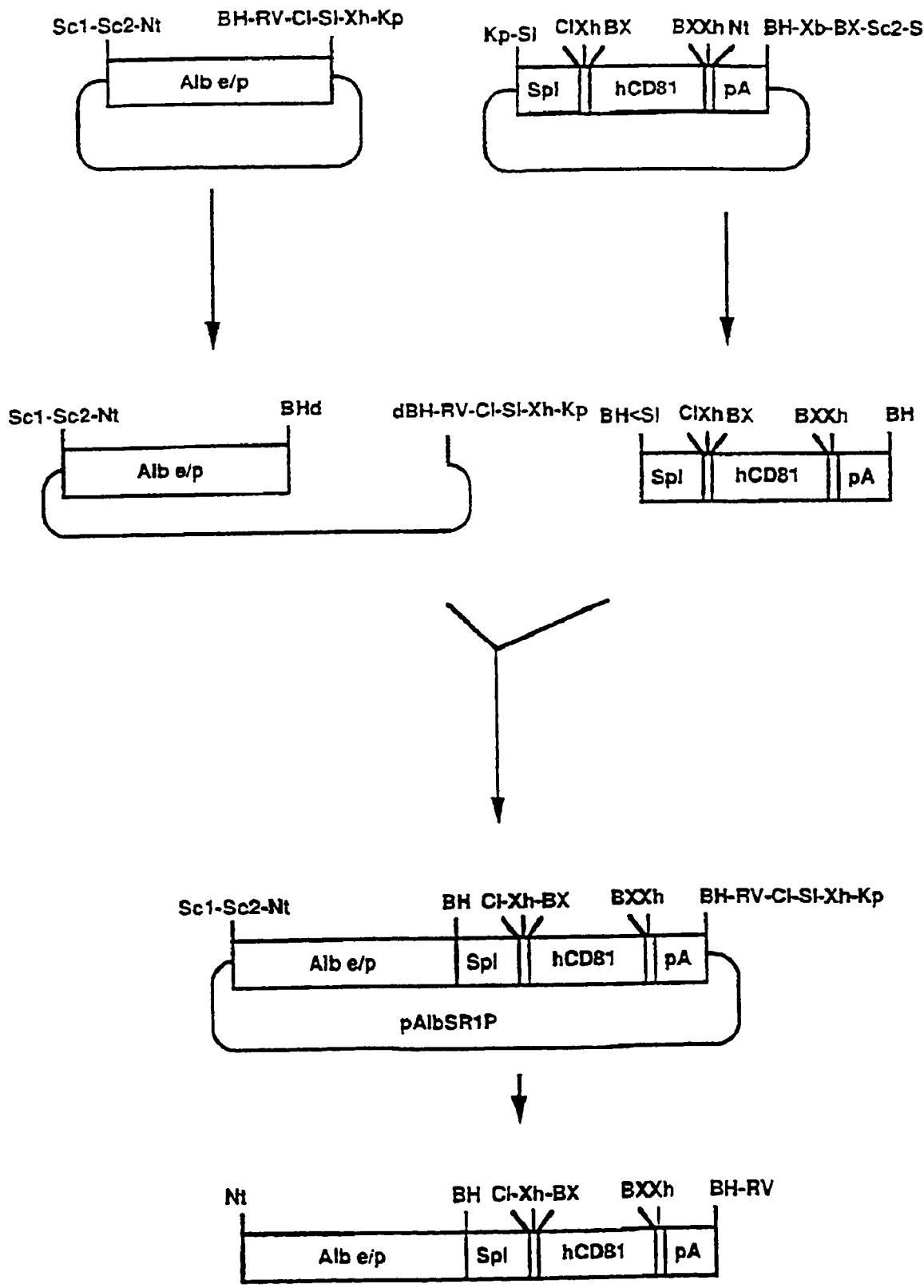
Figure 16:
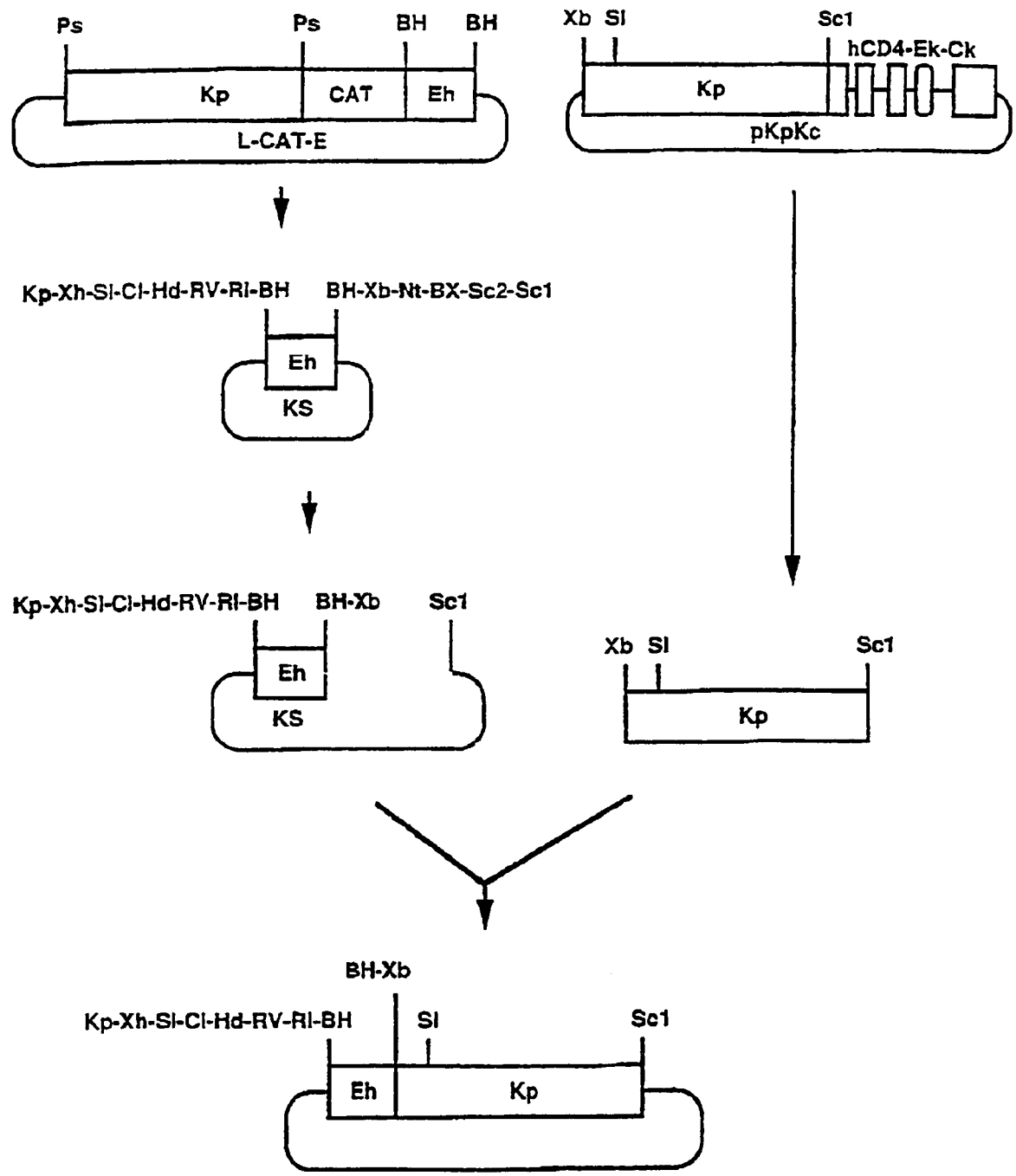
Figure 17:
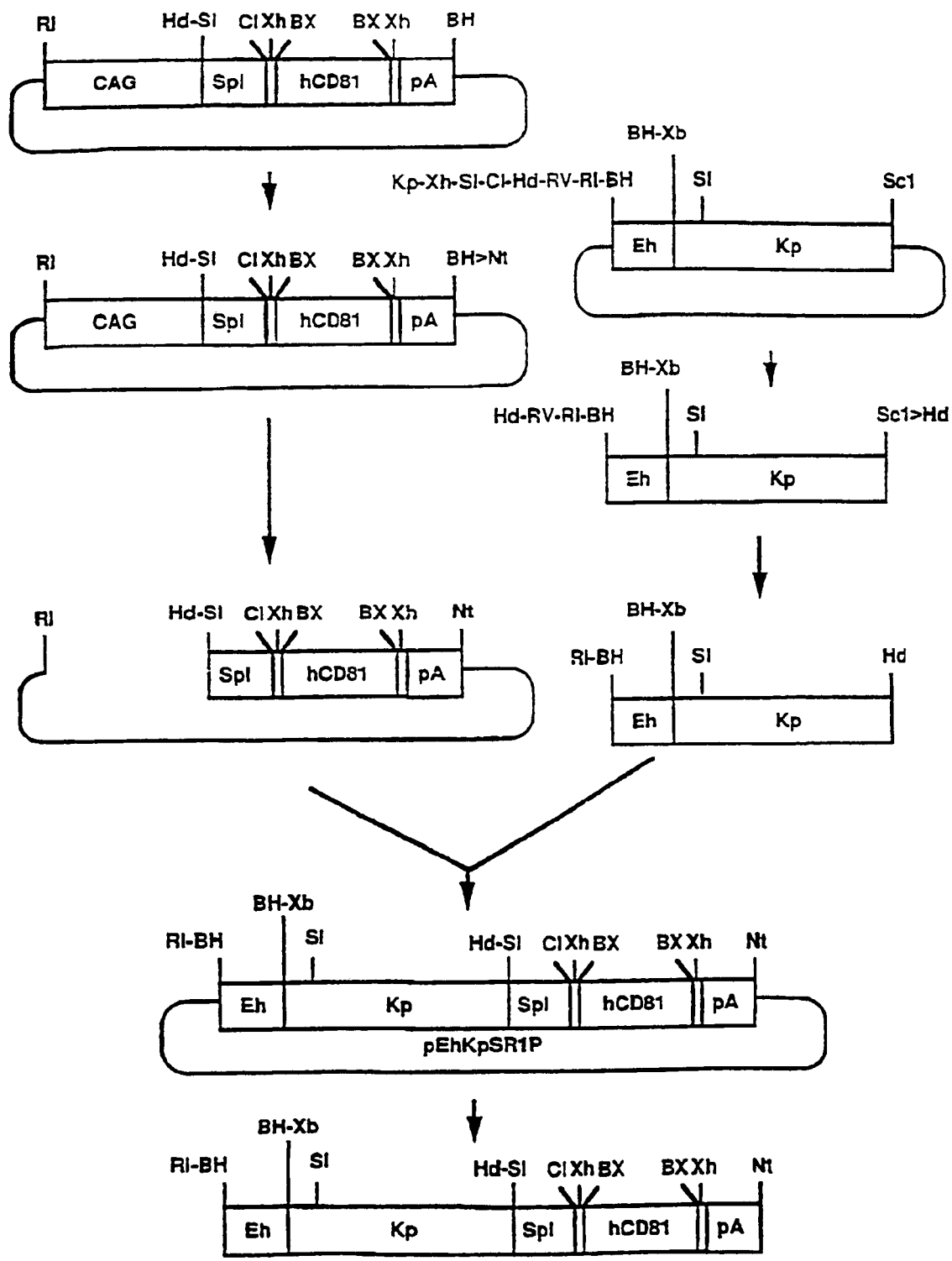

700 bp BamHI fragment of the mouse immunoglobulin heavy chain enhancer (a kind gift from Dr. A. Kudo, Basel Institute for Immunology) and 2.3 kb XbaI-SacI fragment of the mouse kappa light chain promoter was subcloned into a pBluescript KSII(+) vector. The SacI site was converted to a HindIII site by HindIII linker ligation described above. The BamHI site of pCAGSR1P was first converted to NotI site. Then the promoter region of the modified pCAGSR1P construct was removed by EcoRI-HindIII restriction digestion and replaced with the immunoglobulin promoter-enhancer fragment. (pEhKpSR1P in FIG. 15) The 5.2 kb EcoRI-BamHI fragment was submitted to zygote injection.

Together, our data indicate that CD81 is an attachment receptor for HCV and may provide new insight into the mechanisms of HCV infection pathogenesis. Since CD81 associates with an activation complex on the surface of B cells the present finding may explain the pathogenesis of HCV associated cryoglobulinemia even if there is no viral replication in B cells. Moreover, the identification of the interaction between HCV and CD81 may help in mapping conserved neutralising epitopes on the virus envelope which should be important to develop effective vaccines and to provide a decoy receptor for viral neutralisation.

The invention claimed is:

1. A method for inhibiting binding of the E2 protein of HCV to human cells comprising administering to a human infected with HCV an amount of a CD81 protein effective to bind HCV, wherein the human CD81 protein is a soluble form of the CD81 protein that comprises amino acids 113–201 of the human CD81 amino acid sequence depicted in SEQ ID NO: 21, and a deletion of one or more of the transmembrane domains selected from the group consisting of:

a) transmembrane domain 1 (TM1) consisting of amino acids 12–35 of the amino acid sequence of SEQ ID NO :21, b) transmembrane domain 2 (TM2) consisting of amino acids 63–84 of the amino acid sequence of SEQ ID NO:2 1, c) transmembrane domain 3 (TM3) consisting of amino acids 89–112 of the amino acid sequence of SEQ ID NO:21, and d) transmembrane domain 4 (TM4) consisting of amino acids 202–224 of the amino acid sequence of SEQ ID NO:21.

2. The method of claim 1, wherein the CD81 protein consists of the sequence of amino acids shown at positions 113–201 of the human CD8l amino acid sequence depicted in SEQ ID NO:21.

* * * * *

SEQUENCE LISTING

<160> NUMBER OF SEQ ID NOS: 21

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence:
      oligodeoxynucleotides

<400> SEQUENCE: 1
ggcgggggtg gatccggggg tggaggctcg agctttgtca acaaggacc                49

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 2

Phe Val Asn Lys Asp
 1               5

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:
      oligodeoxynucleotides

<400> SEQUENCE: 3
ccccaagctt tcacagcttc ccggagaaga ggtcatcg                            38

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: peptide

<400> SEQUENCE: 4

Leu Lys Gly Ser Phe Leu Asp Asp
 1               5

```
<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence:
      oligodeoxynucleotides

<400> SEQUENCE: 5
caaaaggaat tctatttgtc aacaaggacc agatcgccaa g                41

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 6

Phe Val Asn Lys Asp Gln Ile Ala Lys
 1               5

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence:
      oligodeoxynucleotides

<400> SEQUENCE: 7
ccccaagctt tcaatgatga tgatgatgat gcagcttccc ggagaag          47

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 8

His His His His His His Leu Lys Gly Ser Phe
 1               5                  10

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligodeoxynucleotides

<400> SEQUENCE: 9
cggttccgca gaccactatg                                        20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      oligodeoxynucleotides

<400> SEQUENCE: 10
tcttcacgca gaaagcgtct a                                      21
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
      oligodeoxynucleotide

<400> SEQUENCE: 11
tgagtgtcgt gcagcctcca gga                                          23

<210> SEQ ID NO 12
<211> LENGTH: 357
<212> TYPE: DNA
<213> ORGANISM: Artificial Sequence
<220> FEATURE:
<223> OTHER INFORMATION: Description of Artificial Sequence: Human EC2
      fragment cloned into pThio-His C

<400> SEQUENCE: 12
gagttcctcg acgctaacct ggccggctct ggatccggtg atgacgatga caaggtacct     60
ggcatgctga gctcgagctt tgtcaacaag gaccagatcg ccaaggatgt gaagcagttc    120
tatgaccagg ccctacagca ggccgtggtg gatgatgacg ccaacaacgc caaggctgtg    180
gtgaagacct ccacgagac gcttgactgc tgtggctcca gcacactgac tgctttgacc    240
acctcagtgc tcaagaacaa tttgtgtccc tcgggcagca acatcatcag caacctcttc    300
aaggaggact gccaccagaa gatcgatgac ctcttctccg ggaagctgtg aaagctt       357

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Deduced
      amino acid sequence of EC2 fragment

<400> SEQUENCE: 13

Glu Phe Leu Asp Ala Asn Leu Ala Gly Ser Gly Ser Gly Asp Asp Asp
  1               5                  10                  15

Asp Lys Val Pro Gly Met Leu Ser Ser Ser Phe Val Asn Lys Asp Gln
             20                  25                  30

Ile Ala Lys Asp Val Lys Gln Phe Tyr Asp Gln Ala Leu Gln Gln Ala
         35                  40                  45

Val Val Asp Asp Ala Asn Asn Ala Lys Ala Val Val Lys Thr Phe
     50                  55                  60

His Glu Thr Leu Asp Cys Cys Gly Ser Ser Thr Leu Thr Ala Leu Thr
 65                  70                  75                  80

Thr Ser Val Leu Lys Asn Asn Leu Cys Pro Ser Gly Ser Asn Ile Ile
                 85                  90                  95

Ser Asn Leu Phe Lys Glu Asp Cys His Gln Lys Ile Asp Asp Leu Phe
            100                 105                 110

Ser Gly Lys Leu
        115

<210> SEQ ID NO 14
<211> LENGTH: 348
<212> TYPE: DNA
<213> ORGANISM: Artificial Sequence
<220> FEATURE:
<223> OTHER INFORMATION: Description of Artificial Sequence: Nucleotide
      sequence of EC20His6 fragment cloned into pGEX-KG

<400> SEQUENCE: 14

```
ctggttccgc gtggatcccc gggaatttcc ggtggtggtg gtggaattct atttgtcaac    60
aaggaccaga tcgccaagga tgtgaagcag ttctatgacc aggccctaca gcaggccgtg   120
gtggatgatg acgccaacaa cgccaaggct gtggtgaaga ccttccacga gacgcttgac   180
tgctgtggct ccagcacact gactgctttg accacctcag tgctcaagaa caatttgtgt   240
ccctcgggca gcaacatcat cagcaacctc ttcaaggagg actgccacca agagatcgat   300
gacctcttct ccgggaagct gcatcatcat catcatcatt gaaagctt              348
```

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Deduced
      amino acid sequence of EC2-His 6 fragment

<400> SEQUENCE: 15

```
Leu Val Pro Arg Gly Ser Pro Gly Ile Ser Gly Gly Gly Gly Ile
 1               5                  10                  15

Leu Phe Val Asn Lys Asp Gln Ile Ala Lys Asp Val Lys Gln Phe Tyr
                20                  25                  30

Asp Gln Ala Leu Gln Gln Ala Val Val Asp Asp Ala Asn Asn Ala
            35                  40                  45

Lys Ala Val Val Lys Thr Phe His Glu Thr Leu Asp Cys Cys Gly Ser
 50                  55                  60

Ser Thr Leu Thr Ala Leu Thr Thr Ser Val Leu Lys Asn Asn Leu Cys
 65                  70                  75                  80

Pro Ser Gly Ser Asn Ile Ile Ser Asn Leu Phe Lys Glu Asp Cys His
                85                  90                  95

Gln Lys Ile Asp Asp Leu Phe Ser Gly Lys Leu His His His His His
            100                 105                 110

His
```

<210> SEQ ID NO 16
<211> LENGTH: 236
<212> TYPE: PRT
<213> ORGANISM: Pan troglodytes

<400> SEQUENCE: 16

```
Met Gly Val Glu Gly Cys Thr Lys Cys Ile Lys Tyr Leu Leu Phe Val
 1               5                  10                  15

Phe Asn Phe Val Phe Trp Leu Ala Gly Gly Val Ile Leu Gly Val Ala
                20                  25                  30

Leu Trp Leu Arg His Asp Pro Gln Thr Thr Asn Leu Leu Tyr Leu Glu
            35                  40                  45

Leu Gly Asp Lys Pro Ala Pro Asn Thr Phe Tyr Val Gly Ile Tyr Ile
 50                  55                  60

Leu Ile Ala Val Gly Ala Val Met Met Phe Val Gly Phe Leu Gly Cys
 65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
```

-continued

```
                115                 120                 125
Gln Ala Leu Gln Gln Ala Val Val Asp Asp Ala Asn Asn Ala Lys
        130                 135                 140
Ala Val Val Lys Thr Phe His Glu Thr Leu Asp Cys Cys Gly Ser Ser
145                 150                 155                 160
Thr Leu Thr Ala Leu Thr Thr Ser Val Leu Lys Asn Asn Leu Cys Pro
                165                 170                 175
Ser Gly Ser Asn Ile Ile Ser Asn Leu Phe Lys Glu Asp Cys His Gln
                180                 185                 190
Lys Ile Asp Asp Phe Phe Ser Gly Lys Leu Tyr Leu Ile Gly Ile Ala
                195                 200                 205
Ala Ile Val Val Ala Val Ile Met Ile Phe Glu Met Ile Leu Ser Met
        210                 215                 220
Val Leu Cys Cys Gly Ile Arg Asn Ser Ser Val Tyr
225                 230                 235
```

<210> SEQ ID NO 17
<211> LENGTH: 236
<212> TYPE: PRT
<213> ORGANISM: Cercopithecus aethiops

<400> SEQUENCE: 17

```
Met Gly Val Glu Gly Cys Thr Lys Cys Ile Lys Tyr Leu Leu Phe Val
1               5                   10                  15
Phe Asn Phe Val Phe Trp Leu Ala Gly Gly Val Ile Leu Gly Val Ala
                20                  25                  30
Leu Trp Leu Arg His Asp Pro Gln Thr Thr Asn Leu Leu Tyr Leu Glu
        35                  40                  45
Leu Gly Asp Lys Pro Ala Pro Asn Thr Ser Tyr Val Gly Ile Tyr Ile
        50                  55                  60
Leu Ile Ala Val Gly Ala Val Met Met Phe Val Gly Phe Leu Gly Cys
65                  70                  75                  80
Tyr Gly Ala Ile Gln Glu Ser Gln Cys Leu Leu Gly Thr Phe Phe Thr
                85                  90                  95
Cys Leu Val Ile Leu Phe Ala Cys Glu Val Ala Ala Gly Ile Trp Gly
                100                 105                 110
Phe Val Asn Lys Asp Gln Ile Ala Lys Asp Val Lys Gln Phe Tyr Asp
                115                 120                 125
Gln Ala Leu Gln Gln Ala Val Val Asp Asp Ala Asn Asn Ala Lys
        130                 135                 140
Ala Val Val Lys Thr Phe His Glu Thr Val Asp Cys Cys Gly Ser Ser
145                 150                 155                 160
Thr Leu Ala Ala Leu Thr Thr Ser Val Leu Lys Asn Asn Leu Cys Pro
                165                 170                 175
Ser Gly Ser Asn Ile Ile Ser Asn Leu Leu Lys Lys Asp Cys His Gln
                180                 185                 190
Lys Ile Asp Asp Phe Phe Ser Gly Lys Leu Tyr Leu Ile Gly Ile Ala
                195                 200                 205
Ala Ile Val Val Ala Val Ile Met Ile Phe Glu Met Ile Leu Ser Met
        210                 215                 220
Val Leu Cys Cys Gly Ile Arg Asn Ser Ser Val Tyr
225                 230                 235
```

<210> SEQ ID NO 18
<211> LENGTH: 236

<212> TYPE: PRT
<213> ORGANISM: Mesocricetus auratus

<400> SEQUENCE: 18

```
Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
                20                  25                  30

Leu Trp Leu Arg His Asp Pro Gln Thr Thr Ser Leu Leu Tyr Leu Glu
            35                  40                  45

Leu Gly Asp Arg Pro Ala Pro Ser Thr Phe Tyr Val Gly Ile Tyr Ile
50                      55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
                100                 105                 110

Phe Val Asn Lys Asp Gln Ile Ala Lys Asp Val Lys Gln Phe Tyr Asp
            115                 120                 125

Gln Ala Leu Gln Gln Ala Val Val Asp Asp Asp Ala Asn Asn Ala Lys
    130                 135                 140

Ala Val Val Lys Thr Phe His Glu Thr Leu Asn Cys Cys Gly Ser Asn
145                 150                 155                 160

Ala Leu Thr Ala Leu Thr Thr Ser Val Leu Lys Asn Ser Leu Cys Pro
                165                 170                 175

Ser Gly Thr Asn Ile Phe Asn Ser Leu Met Lys Glu Asp Cys His Gln
            180                 185                 190

Lys Ile Asp Glu Leu Phe Ser Gly Lys Leu Tyr Leu Ile Gly Ile Ala
    195                 200                 205

Ala Ile Val Val Ala Val Ile Met Ile Phe Glu Met Ile Leu Ser Met
210                 215                 220

Val Leu Cys Cys Gly Ile Arg Asn Ser Ser Val Tyr
225                 230                 235
```

<210> SEQ ID NO 19
<211> LENGTH: 236
<212> TYPE: PRT
<213> ORGANISM: Rattus norvegicus

<400> SEQUENCE: 19

```
Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
                20                  25                  30

Leu Trp Leu Arg His Asp Pro Gln Thr Thr Thr Leu Leu Tyr Leu Glu
            35                  40                  45

Leu Gly Asp Lys Pro Ala Pro Ser Thr Phe Tyr Val Gly Ile Tyr Ile
50                      55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
                100                 105                 110
```

Phe Val Asn Lys Asp Gln Ile Ala Lys Asp Val Lys Gln Phe Tyr Asp
            115                 120                 125

Gln Ala Leu Gln Gln Ala Val Met Asp Asp Ala Asn Asn Ala Lys
130                 135                 140

Ala Val Val Lys Thr Phe His Glu Thr Leu Asn Cys Cys Gly Ser Asn
145                 150                 155                 160

Thr Leu Thr Thr Leu Thr Thr Ala Val Leu Arg Asn Ser Leu Cys Pro
                165                 170                 175

Ser Ser Ser Asn Ser Phe Thr Gln Leu Leu Lys Glu Asp Cys His Gln
            180                 185                 190

Lys Ile Asp Glu Leu Phe Ser Gly Lys Leu Tyr Leu Ile Gly Ile Ala
            195                 200                 205

Ala Ile Val Val Ala Val Ile Met Ile Phe Glu Met Ile Leu Ser Met
210                 215                 220

Val Leu Cys Cys Gly Ile Arg Asn Ser Ser Val Tyr
225                 230                 235

<210> SEQ ID NO 20
<211> LENGTH: 236
<212> TYPE: PRT
<213> ORGANISM: Mus musculus

<400> SEQUENCE: 20

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Ser Leu Leu Tyr Leu Glu
        35                  40                  45

Leu Gly Asn Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
            115                 120                 125

Gln Ala Leu Gln Gln Ala Val Met Asp Asp Ala Asn Asn Ala Lys
130                 135                 140

Ala Val Val Lys Thr Phe His Glu Thr Leu Asn Cys Cys Gly Ser Asn
145                 150                 155                 160

Ala Leu Thr Thr Leu Thr Thr Ile Leu Arg Asn Thr Leu Cys Pro
                165                 170                 175

Ser Gly Gly Asn Ile Leu Thr Pro Leu Leu Gln Gln Asp Cys His Gln
            180                 185                 190

Lys Ile Asp Glu Leu Phe Ser Gly Lys Leu Tyr Leu Ile Gly Ile Ala
            195                 200                 205

Ala Ile Val Val Ala Val Ile Met Ile Phe Glu Met Ile Leu Ser Met
210                 215                 220

Val Leu Cys Cys Gly Ile Arg Asn Ser Ser Val Tyr
225                 230                 235

<210> SEQ ID NO 21

-continued

```
<211> LENGTH: 236
<212> TYPE: PRT
<213> ORGANISM: Artificial Sequence
<220> FEATURE:
<223> OTHER INFORMATION: Description of Artificial Sequence:
      description

<400> SEQUENCE: 21

Met Gly Val Glu Gly Cys Thr Lys Cys Ile Lys Tyr Leu Leu Phe Val
  1               5                  10                  15

Phe Asn Phe Val Phe Trp Leu Ala Gly Gly Val Ile Leu Gly Val Ala
             20                  25                  30

Leu Trp Leu Arg His Asp Pro Gln Thr Thr Asn Leu Leu Tyr Leu Glu
         35                  40                  45

Leu Gly Asp Lys Pro Ala Pro Asn Thr Phe Tyr Val Gly Ile Tyr Ile
     50                  55                  60

Leu Ile Ala Val Gly Ala Val Met Met Phe Val Gly Phe Leu Gly Cys
 65                  70                  75                  80

Tyr Gly Ala Ile Gln Glu Ser Gln Cys Leu Leu Gly Thr Phe Phe Thr
                 85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Asp Ala Asn Asn Ala Lys
    130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235
```